US009011948B2

(12) United States Patent
Dekker et al.

(10) Patent No.: US 9,011,948 B2
(45) Date of Patent: Apr. 21, 2015

(54) ENZYME PREPARATIONS YIELDING A CLEAN TASTE

(75) Inventors: Petrus Jacobus Theodorus Dekker, The Hague (NL); Luppo Edens, Rotterdam (NL); Maximiliaan Peter Marie De Swaaf, Gouda (NL); Albertus Alard Van Dijk, Vlaardingen (NL)

(73) Assignee: DSM IP Assets B.V., Heerlen (NL)

( * ) Notice: Subject to any disclaimer, the term of this patent is extended or adjusted under 35 U.S.C. 154(b) by 205 days.

(21) Appl. No.: 12/094,541

(22) PCT Filed: Nov. 28, 2006

(86) PCT No.: PCT/EP2006/068979
§ 371 (c)(1),
(2), (4) Date: May 21, 2008

(87) PCT Pub. No.: WO2007/060247
PCT Pub. Date: May 31, 2007

(65) Prior Publication Data
US 2008/0286412 A1 Nov. 20, 2008

(30) Foreign Application Priority Data

Apr. 25, 2006 (EP) .................................. 06113062
Nov. 28, 2006 (EP) .................................. 05111392

(51) Int. Cl.
*A23C 9/12* (2006.01)
*A23C 21/02* (2006.01)
*A23C 23/00* (2006.01)
*C12N 9/26* (2006.01)
*C12N 15/00* (2006.01)
*C12N 9/38* (2006.01)
*C12N 9/62* (2006.01)
*C12N 9/16* (2006.01)

(52) U.S. Cl.
CPC ............ *C12N 9/2468* (2013.01); *A23C 9/1206* (2013.01); *C12N 9/62* (2013.01); *C12Y 302/01023* (2013.01); *C12N 9/16* (2013.01); *C12N 9/2471* (2013.01); *C12Y 301/06001* (2013.01)

(58) Field of Classification Search
USPC .................................. 426/34, 35, 36, 42, 61
See application file for complete search history.

(56) References Cited

U.S. PATENT DOCUMENTS

| 3,737,377 | A | 6/1973 | Sternberg | |
| 5,093,137 | A * | 3/1992 | Shazer et al. | 426/42 |
| 6,784,168 | B1 * | 8/2004 | Jones et al. | 514/76 |
| 6,972,282 | B1 * | 12/2005 | Tossavainen et al. | 514/15.7 |
| 2002/0146499 | A1 | 10/2002 | Valli et al. | |
| 2002/0182298 | A1 * | 12/2002 | Lindsay | 426/534 |
| 2004/0121014 | A1 * | 6/2004 | Guo et al. | 424/471 |
| 2006/0003051 | A1 * | 1/2006 | Cleary et al. | 426/36 |

FOREIGN PATENT DOCUMENTS

| WO | 02/060268 | 8/2002 |
| WO | 02/081673 | 10/2002 |
| WO | 2005/074695 | 8/2005 |
| WO | 2006/009938 | 1/2006 |

OTHER PUBLICATIONS

NPL Lopez et al., J Agric. Food Chem. 41: 446-454, 1993.*
NPL Off-flavor retrieved on Oct. 7, 2013.*
NPL Koch A.K. et al. In Biotechnology pp. 1335-1339, 1988.*
International Search Report for PCT/EP2006/068979 dated Dec. 27, 2007.
Kim et al. "Expression and characterization of *Kluyveromyces lactis* beta-galactosidase in *Escherichia coli*," Biotechnology Letters, vol. 25, No. 20, pp. 1769-1774, Oct. 2003.
Becerra et al. "Micro-scale purification of beta-galactoidase from *Kluyveromyces lactis* reveals that dimeric and tetrameric forms are active," Biotechnology Letters, vol. 12, No. 3, pp. 253-256, Mar. 1998.
Beil et al. "Purification and characterization of the arylsulfatase, synthesized by *Pseudomonas aeruginosa* PAO during growth in sulfate-free medium and cloning of the arylsulfatase gene (atsA)," European Journal of Biochemistry, vol. 229, No. 2, pp. 385-394, 1995.
Mittal et al. "The effect of protease contamination in lactase on the flavour of lactose-hydrolyzed milks," Australian Journal of Dairy Technology, Dairy Industry Association of Australia, Melbourne, AU, vol. 46, No. 1, pp. 46-48, May 1991.
Lopez et al. "Metabolic conjugates as precursors for characterizing flavor compounds in ruminant milks," Journal of Agricultural and Food Chemistry, American Chemical Society, Washington, vol. 41, No. 3, pp. 446-454, Mar. 1993.
Gekas et al. "Hydrolysis of lactose a literature review," Process Biochemistry, vol. 20, No. 1, 1985, pp. 2-12.
"Lactase: an optimum enzyme for low lactose dairy products," Asia Pacific Food Industry (Supplement) pp. 24-27, Jun. 2001.
Hatanaka et al. "Two glycosulfatases from the liver of a marine gastropod, *Charonia lampasch*," Journal of Biochemistry, vol. 79, No. 1, pp. 27-34, 1976.
"Lactase (neutral) (beta-galactosidase) activity," Food Chemical Codex 4th Edition, pp. 801-802, Jul. 1996.
Dal et al. "Purification and characterization of two serine carboxypeptidases from *Aspergillus-niger* and their use in C-terminal sequencing of proteins and peptide synthesis," Applied and Environmental Microbiology, vol. 58, No. 7, pp. 2144-2152, 1992.
Fulop et al. "Prolyl oligopeptidase: An unusual beta-propeller domain regulates proteolysis," Cell, vol. 94, No. 2, pp. 161-170, Jul. 1998.
Edens et al. "Extracellular prolyl endoprotease from *Aspergillus niger* and its use in the debittering of protein hydrolysates" Journal of Agricultural and Food Chemistry, vol. 53, No. 20, pp. 7950-7957, Oct. 2005.

(Continued)

Primary Examiner — Michele L Jacobson
Assistant Examiner — Bhaskar Mukhopadhyay
(74) Attorney, Agent, or Firm — Miles & Stockbridge PC

(57) ABSTRACT

Process for producing a dairy product by adding a lactase to a dairy product which contains lactose, the lactase added having less than 40 units arylsulfatase activity per NLU of lactase activity.

25 Claims, 7 Drawing Sheets

(56) References Cited

OTHER PUBLICATIONS

Australia Patents Act 1990: New Zealand Patent No. 593948, ("the opposed Application") in the name of DSM IP Assets Pty B.V. ("the Applicant") Opposition to grant thereof by DuPont Nutrition Aps. ("the Opponent"); Exhibit DK-1-2.
Australia Patents Act 1990: New Zealand Patent No. 593948, ("The opposed Application") in the name of DSM IP Assets Pty B.V.. ("the Applicant"); Exhibit DK-3: Dunn et al., "Evaluation of the Role of Microbial Strecker-Derived Aroma Compounds in Unclean-Type Flavors of Cheddar Cheese."
Australia Patents Act 1990: New Zealand Patent No. 593948, ("the opposed Application") in the name of DSM IP Assets Pty B.V.. ("the Applicant"); Exhibit DK-4: Kilic et al., "Arylsulphatase activity in milk and rennet from differend sources." International Diary Journal; 16 (2006) 88-91.
Australia Patents Act 1990: New Zealand Patent No. 593948, ("the opposed Application") in the name of DSM IP Assets Pty B.V.. ("the Applicant"): Exhibit DK-5: Badings et al., "Phenolic Flavor in Cheese;" Netherlands Institute for Dairy Research, Ede.
Australia Patents Act 1990: New Zealand Patent No. 593948, ("The opposed Application") in the name of DSM IP Assets Pty B.V. ("the Applicant"); Exhibit DK-6: Marschke et al., "The Effect of Partial Lactose Hydrolysis on the Manufacture and Ripening of Cheddar Cheese;" The Australian Journal of Diary Technology; Dec. 1978.
Australia Patents Act 1990: New Zealand Patent No. 593948, ("the opposed Application") in the name of DSM IP Assets Pty B.V. ("the Applicant"); Exhibit DK-7: "Enzyme Preparations Yielding a Clean Taste;" WO 2007/060247; PCT/2006/068979.
First Statutory Declaration by Morten Krog Larsen of Jul. 11, 2014 together with Exhibits MKL-1 to MKL-5.
Second Statutory Declaration by Morten Krog Larsen of Jul. 11, 2014 together with Exhibits MKL-6 and MKL-7.
Statutory Declaration by Marie-Laure Delabre of Jul. 17, 2014 together with Exhibits MLD-1 to MLD-8.
Statutory Declaration by Derek Knighton of Jul. 18, 2014 together with Exhibits DK1 to DK7.
Opposition to EP-B-1954808, "Enzyme preparation yielding a clean taste," in the name of DSM IP Assets B.V., by DuPont Nutrition Biosciences ApS. X103951EP/G0861.
Opposition to EP 1 954 808/06 819 802.7, "Enzyme preparation yielding a clean taste," DSM IP Assets B.V., in the name of by Novozymes A/S. Oct. 1, 2014.
Hussein et al; "Reduction of Lactose in Milk by Purified Lactase Produced by *Kluyveromyces lactis*"; Journal of Food Protection; Jan. 1988; vol. 52; No. 1; pp. 30-34; International Association of Milk, Food and Environmental Sanitarians.
Kilic et al.; "Arylsulphatase activity in milk and rennet from different sources"; International Dairy Journal; 2006; 16; pp. 88-91; Elsevier.
Kitchen; "Enzymic methods for estimation of the somatic cell count in bovine milk"; Journal of Dairy Research; 1976; vol. 43; pp. 251-258.
GE Healthcare Data File 18-1172-87 AC; Phenyl Sepharose High Performance Butyl Sepharose High Performance; 2007.
Mittal et al.; "The effect of Protease Contamination In Lactase on the Flavour of Lactose-Hydrolyzed Milks"; The Australian Journal of Dairy Technology; May 1991; pp. 46-48.
Weiqun et al.; "Purification and Charaterization of Beta-galactosidase from *Kluyveromyces lactis*"; Chinese Journal of Bacteriology; 1993; vol. 9; No. 4; pp. 348-354 (Chinese language).
Weiqun et al.; "Purification and Charaterization of Beta-galactosidase from *Kluyveromyces lactis*"; Chinese Journal of Bacteriology; 1993; vol. 9; No. 4; pp. 348-354 (English translation).
Affinity Chromatography; Principles and Methods, Amersham Biosciences, 2002; first seven pages, and pp. 47-51 and 88-92, as well as last two pages.
Third Party Observation in European Patent Application No. 1954808 dated Oct. 8, 2012.
Third Party Observation in European Patent Application No. 1954808 dated Feb. 3, 2012.
Third Party Observation in European Patent Application No. 1954808 dated Jan. 24, 2012.
Third Party Observation in European Patent Application No. 1954808 dated Jul. 20, 2011.
Third Party Observation in European Patent Application No. 1954808 dated Jul. 1, 2011.
Third Party Observation in European Patent Application No. 1954808 dated Aug. 6, 2010.
Third Party Observation in European Patent Application No. 1954808 dated Mar. 30, 2010.
Exhibit PH-1: Peter Hobman's Curriculum vitae.
Exhibit PH-2: Peter Hobman's Curriculum vitae-Publications.
Exhibit PH-3:Divisional Application of New Zealand Application No. 568554.
Exhibit PH-4: Federal Court of Australia Practice Note CM 7, Expert Witnesses in Proceedings in the Federal Court of Australia, issued Aug. 1, 2011.
Exhibit PH-5: J. Greig Zadow: Whey and Lactose Processing: "Lactose Hydrolysis," Chapter 10. pp. 361-408.
Exhibit PH-6: P.G. Hobman, "Review of Processes and Products for Utilization of Lactose in Deproteinated Milk Serum," Journal of Dairy Science, 67:11, pp. 2360-2653 (1984).
Statutory Declaration of Peter Hobman executed Feb. 16, 2015.

\* cited by examiner

SEQUENCE LISTING

```
<160> NUMBER OF SEQ ID NOS: 7

<210> SEQ ID NO 1
<211> LENGTH: 30
<212> TYPE: DNA
<213> ORGANISM: Artificial Sequence
<220> FEATURE:
<223> OTHER INFORMATION: primer DFS-15289

<400> SEQUENCE: 1
tcgccgcggt tgtcaactat attaactatg                                        30

<210> SEQ ID NO 2
<211> LENGTH: 24
<212> TYPE: DNA
<213> ORGANISM: Artificial Sequence
<220> FEATURE:
<223> OTHER INFORMATION: primer DFS-15290

<400> SEQUENCE: 2
gatagatcat agagtaacaa ttgg                                              24

<210> SEQ ID NO 3
<211> LENGTH: 23
<212> TYPE: DNA
<213> ORGANISM: Artificial Sequence
<220> FEATURE:
<223> OTHER INFORMATION: primer DFS-15291

<400> SEQUENCE: 3
gcaactgaag gtggtatcaa ttg                                               23

<210> SEQ ID NO 4
<211> LENGTH: 28
<212> TYPE: DNA
<213> ORGANISM: Artificial Sequence
<220> FEATURE:
<223> OTHER INFORMATION: ptimer DFS-15292

<400> SEQUENCE: 4
cacccgcggc accagataat ggaggtag                                          28
```

```
<210> SEQ ID NO 5
<211> LENGTH: 20
<212> TYPE: DNA
<213> ORGANISM: Artificial Sequence
<220> FEATURE:
<223> OTHER INFORMATION: primer DFS-15340

<400> SEQUENCE: 5
cggcaccaga taatggaggt                                              20

<210> SEQ ID NO 6
<211> LENGTH: 24
<212> TYPE: DNA
<213> ORGANISM: Artificial Sequence
<220> FEATURE:
<223> OTHER INFORMATION: primer Fw 3?amdS

<400> SEQUENCE: 6
gacaattgat accaccttca gttg                                         24

<210> SEQ ID NO 7
<211> LENGTH: 23
<212> TYPE: DNA
<213> ORGANISM: Artificial Sequence
<220> FEATURE:
<223> OTHER INFORMATION: primer Rv downstream

<400> SEQUENCE: 7
ctgggaaatg tggtgactcc ata                                          23
```

ENZYME PREPARATIONS YIELDING A CLEAN TASTE

This application is the U.S. national phase of International Application No. PCT/EP2006/068979, filed 28 Nov. 2006, which designated the U.S. and claims priority to European Application No. 05111392.6 filed 28 Nov. 2006 and European Application No. 06113062.1 filed 25 Apr. 2006; the entire contents of each of which are hereby incorporated by reference.

FIELD OF THE INVENTION

The invention relates to a process for treating a substrate with an enzyme preparation, to a new enzyme preparation and a process for preparing an enzyme preparation. The invention also relates to lactase.

BACKGROUND OF THE INVENTION

The use of enzymes to improve the chemical, physico-chemical or organoleptic nature of food grade products is wide spread. Also in the processing of cow milk and other animal derived substrates, the use of enzymes adds significant value to the end product. Examples are incubations with lactase to render milk acceptable for lactose intolerant individuals, proteolytic hydrolysis of casein and whey proteins to alleviate allergenicities and to improve foam characteristics, the modification of egg phospholipids using phospholipase A2 to improve baking performance and stabilize mayonaises, the use of transglutaminases on meat and fish products to improve hardness and elasticity as well as the removal of oxygen from egg products or grated cheese by adding glucose oxidase. Additionally, enzyme treatments are being used to enhance the flavor of various animal derived food products. For example, proteases are being used to speed up flavour development in fish and meat extracts. Furthermore, accelerating flavor development in cheese is a well known target. Whereas EMC (Enzyme Modified Cheese) is an established product in which primarily various lipases are used, speeding up the subtle taste changes involved in the aging of cheeses by adding minor quantities of exoproteases, lipases or esterases, is a more recent development.

The invention also relates to lactase. Lactase or β-galactosidase (E.C: 3.2.1.23) is an enzyme, which catalyzes the hydrolysis of lactose (a disaccharide) into its component monosaccharides glucose and galactose. Lactose is present in dairy products and more specifically in milk, skimmed milk, cream and other milk products. The breakdown of lactose occurs in the intestinal wall of the human body (and other mammals) by the natural presence of lactase.

The nutritional and functional problems caused by lactose in most populations that lack lactase are well known and described. Members of such populations cannot hydrolyze the lactose, which in such cases passes into the large intestine, where it produces dehydration, poor calcium absorption, diarrhea, flatulence, belching and cramps, and, in severe cases, even watery explosive diarrhea.

An important industrial application of lactase is in the production of lactose-hydrolyzed milk products for lactose intolerant individuals. Such hydrolysed milk products include pasteurized milk, UHT-milk and milk reconstituted from all or part of its original constituents with or without intermediate processing steps such as protein hydrolysis. Treatment with lactase may be done prior to and after the heat-treatment of the milk. The lactase treatment may be done by adding the enzyme to the milk. The solubility properties of lactose are such that it may lead to its crystallization, leading to a sandy or gritty texture. Such undesired texture may be found in some dairy products such as condensed milk, evaporated milk, dry milk, frozen milk, ice cream, and in confectionery products with a high content of milk. Full or partial hydrolysis of lactose by lactase eliminates this problem, providing products with a homogeneous texture and as a result a higher consumer acceptance.

Another industrial application of lactase is to increase sweet taste in lactose containing products like milk or yoghurt. The hydrolysis of lactose in such products results in increased sweet taste as a result of the production of glucose. Another industrial application of lactase is the hydrolysis of lactose products containing dairy components such as bread. Lactose is added in such products to enhance flavour, retain moisture, provide browning and improve toasting properties. Hydrolyzed lactose syrups are promising in terms of e.g. enhancing crust-colour development, improving flavour and aroma, modifying texture, extending shelf life and strengthening loaf structure.

Lactose hydrolysis by lactase in fermented milk products such as yoghurt will increase sweet taste. However, when the lactase is added prior to the beginning of the fermentative process, it may increase the rate of acid development and thus reduce processing times. The lactase treatment of milk or milk-derived products such as whey makes such products suitable for application in animal feed and pet food for lactose intolerant animals such as cats. The lactose hydrolysis allows the manufacture of a higher concentrated whey and at the same time prevents gut problems, similar to those described earlier for lactose-deficient patients. Lactose hydrolyzed whey is concentrated to produce a syrup containing 70-75% solids and is used as a food ingredient in ice cream, bakery and confectionery products.

Lactases have been described for and isolated from a large variety or organisms, including micro-organisms. Lactase is often an intracellular component of micro-organisms like *Kluyveromyces* and *Bacillus. Kluyveromyces* and especially *K. fragilis* and *K. lactis*, and other yeasts such as those of the genera *Candida, Torula* and *Torulopsis* are a common source of yeast enzymes lactases, whereas *B. coagulans* or *B circulans* are well known sources for bacterial lactases. Several commercial lactase preparations, derived from these organisms are available such as Maxilact® (from *K. lactis*, produced by DSM, Deflt, The Netherlands). All these lactases are so called neutral lactases since they have a pH optimum between pH=6 and pH=8. Several organisms such as *Aspergillus niger* and *Aspergilus oryzae* can produce extra-cellular lactase, and U.S. Pat. No. 5,736,374 describes an example of such lactase, produced by *Aspergilllus oryzae*. The enzymatic properties of lactases like pH- and temperature optimum vary between species. In general, however, lactases that are excreted show a lower pH-optimum of pH=3.5 to pH=5.0; intracellular lactases usually show a higher pH optimum in the region of pH=6.0 to pH=7.5, but exceptions on these general rules occur. The choice for a neutral or acidic lactase depends on the pH profile in the application. In applications with neutral pH, neutral lactases are usually preferred; such applications include milk, ice cream, whey, cheese, yoghurt, milk powder etc. Acid lactases are more suited for applications in the acidic range. The appropriate lactase concentration is dependent on the initial lactose concentration, the required degree of hydrolysis, pH, temperature and time of hydrolysis.

Although aimed at improving the functionality and/or taste profiles of the food product, occasionally an enzyme treatment can have unexpected and undesirable side effects. An example of an undesirable side effect is the development of off-flavor as a result of the enzyme treatment.

Mettall et. al, The Australian Journal of Dairy Technology, (1991), 46-48 describes the problem of off-flavor development when milk is treated with lactase. According to this publication high levels of protease will result in the rapid development of off-flavors. Production processes are therefore optimised to minimize proteolytic side activities in order to reduce the risk of off-flavour formation. An example of a purification process for *K. lactis* derived lactase is described in WO 02/081673.

It is found that even lactase preparations with low protease activity can still give rise to off-flavour formation. This is especially the case for the neutral lactases, derived from the cytoplasm of yeast. The off-flavour formation that is associated with the use of lactase preparations is especially critical for lactose hydrolysed UHT-milk. The lactases that are used in this case are neutral lactases because of their favourable pH optimum for milk. The UHT milk has received a high heat treatment to obtain a shelf life of several months at room temperature. The long storage times outside the refrigerator make these products especially prone to off-flavour formation: even a very low off-flavour formation rate can give rise to significant off-flavour formation after several months of storage, making the product unattractive for consumption.

SUMMARY OF THE INVENTION

Surprisingly it is now found that the presence of arylsulfatase as contaminating side activity in enzyme preparations, even at very low levels, can lead to a strong development of off-flavor in a product when a substrate is treated with the preparation, and that the use of an enzyme preparation having no or a reduced aryl sulfatase activity results in a strong reduction of off-flavor development.

Accordingly, the invention provides a process, in one aspect, a process comprising treating a substrate with an enzyme preparation, wherein the enzyme preparation is substantially free from arylsulfatase.

The invention also provides, in further aspects, enzyme preparations substantially free from arylsulfatase.

The invention also provides, in a particular aspect, lactase which comprises less than 40 units arylsulfatase activity per NLU of lactase activity.

The lactase preparation according to the invention may advantageously be used in food and feed products to hydrolyse lactose without the formation of off-flavour compounds.

We have surprisingly found that aryl-sulfatase is a crucial enzyme activity, responsible for off-flavor formation. We have found confirmative evidence by adding aryl-sulfatase to UHT-milk and which resulted in that this single enzyme is capable to mimic the off-flavour often observed in lactase-treated UHT-milk.

Without wishing to be bound by any scientific theory, it is believed that hydrolysis of metabolic conjugates, in particular alkyl phenols substituted with a sulfate group, by arylsulfatases is a mechanism resulting in the development of off-flavor. Accordingly, the enzyme preparations according to the invention are particular advantageous for the treatment of substrates containing an alkyl phenol substituted with a sulphate group.

DETAILED DESCRIPTION OF THE INVENTION

In one aspect, the invention provides a lactase which comprises less than 40 units arylsulfatase activity per NLU of lactase activity. Preferably, the lactase comprises less than 30 units arylsulfatase activity per NLU of lactase activity, more preferably less than 20 units arylsulfatase activity per NLU of lactase activity and most preferably less than 10 units arylsulfatase activity per NLU of lactase activity. The aryl-sulfatase units are defined in example 2 and are normalized for lactase activity expressed in NLU and also defined in example 2.

The lactase may be an intracellular or an extracellular produced lactase. In a preferred embodiment, the lactase is intracellular produced lactase.

In a preferred embodiment, the lactase is a neutral lactase. The neutral lactase may have a pH optimum between pH=6 and pH=8.

Neutral lactase preparations are usually derived from the cytoplasm of micro-organisms. Their production includes the (large scale) fermentation of the micro-organism, followed by isolation of the lactase. The latter requires the disruption of the cell wall in order to release the enzyme from the cytoplasm. Several techniques can be used to obtain cell lysis, including permeabilization of the cell wall by organic solvents such as octanol, sonication or French Pressing. Other enzymes beside lactase are released at the same time from the cytoplasm, including proteases.

In a preferred embodiment, the lactase has less than 0.5 RFU/min protease activity per NLU of lactase activity.

The intracellular lactases which can be purified according to the present invention have been described for and isolated from a large variety or organisms, including microorganisms. Lactase is often an intracellular component of micro-organisms like *Kluyveromyces* and *Bacillus*. *Kluyveromyces* and especially *K. lactis, K. marxinus* and *K. fragilis*, and other yeasts such as those of the genera *Candida, Torula* and *Torulopsis* are a common source of yeast enzymes lactases, whereas *B. coagulans* or *B circulans* are well known sources for bacterial lactases. Several commercial lactase preparations, derived from these organisms are available such as Maxilact® (from *K. lactis*, produced by DSM). All these lactases are so called neutral lactases since they have a pH optimum between pH=6 and pH=8.

Intracellular lactases have been described for various species, and for several of them their amino acid sequences and/or their DNA sequences are known. The sequence information is publicly available in sequence databases, for example in GenBank (Bethesda, Md. USA), European Molecular Biology Laboratory's European Bioinformatics Institute (EMBL-Bank in Hinxton, UK), the DNA Data Bank of Japan (Mishima, Japan) and the Swissprot (Switzerland). Lactases can be identified in genomes based on homology in either the gene and/or protein sequences. Crude preparations of intracellular enzymes are characterized by the presence of several enzymes only occurring in the cytoplasm of the cell, such as the enzymes involved in the central metabolism of the cell, including those involved in glycolysis.

Extracellular lactases have also been described. They are generally recognized as extracellular enzymes because they contain a peptide sequence called leader sequence. This leader sequence is recognized in some way by the cell that produces the enzymes as a signal that the enzyme should be exported out of the cell. During secretion, the leader sequence is usually removed. Extracellular lactases have been described for various species, e.g. *Aspergillus oryzae*. Crude preparations of extracellular lactases are characterized by the absence of intracellular enzymes and the presence of typical extracellular enzymes like proteases. The type of extracellular enzymes found varies with the organism and are typical for that organism. Due to cell lysis during fermentation or processing, low levels of intracellular enzymes can be found in such extracellular enzyme preparations.

Lactase enzymes can thus be classified as extracellular or intracellular based on comparison of their amino acid sequence with those of other known lactases. In principle, an intracellular lactase can be provided with a leader sequence. This could result in excretion of the lactase from the cell into the medium. Crude preparations of such enzymes would be characterized by a lactase, classified as intracellular on basis of its amino acid sequence, in the presence of typical extracellular enzymes and absence or low levels of typical intracellular enzymes.

Preferred intracellular lactases used in the present invention are: *K. lactis* lactase having an amino acid sequence as described in http://www.ebi.uniprot.org/entry/BGAL_K-LULA or a lactase having an amino acid sequence which is at least 90%, preferably at least 95% identical with the amino acid sequence of *K. lactis*. *K. marxianus* lactase having an amino acid sequence as described in http://www.ebi.uniprot.org/entry/Q6QTF4_KLUMA or a lactase having an amino acid sequence which is at least 90%, preferably at least 95% identical with the amino acid sequence of *K. lactis*. *B. circulans* lactase having an amino acid sequence as described in
http://www.ebi.uniprot.org/uniprot-srv/uniProtView.do?proteinId=O31341_BACCI&pager.offset=0
http://www.ebi.uniprot.org/uniprot-srv/uniProtView.do?proteinId=Q45092_BACCI&pager.offset=0
http://www.ebi.uniprot.org/uniprot-srv/uniProtView.do?proteinId=Q45093_BACCI&pager.offset=0
or a lactase having an amino acid sequence which is at least 90%, preferably at least 95% identical with the amino acid sequence of *B. circulans*.

The terms "homology" or "percent identity" are used interchangeably herein. It is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The preparation of intracellular lactases requires the disruption of the cells to release the lactase enzyme. At the same time, other cytoplasmic enzymes are released. The quality of an industrial preparation of the lactase is determined by ratio of side activities to lactase activity. Especially proteases are critical side enzymes since they are known to lead to unwanted side effects in application, such as milk clotting or off-flavour formation in milk. Off-flavour formation is especially critical in products with a long shelf life and which are stored at room temperatures. One such product is UHT-milk, and off-flavour formation is a known problem for lactose hydrolysed UHT-milk. The UHT-milk is very sensitive to off-flavour formation; when a lactase preparation does not generate off-flavour in UHT-milk, it will usually also not generate off-flavour in other applications. Compounds associated with off-flavour formation in milk, and especially UHT-milk, are related to both proteolysis and Maillard reactions (Valero et al (2001) *Food Chem*. 72, 51-58). Any proteases present as side activities in lactase preparations potentially enhance the off-flavour formation; it is unclear what levels of proteases are required, but with storage times of several months even very low proteolytic activity could be important. The UHT-milk is very sensitive to off-flavour formation; when a lactase preparation does not generate off-flavour in UHT-milk, other than the off-flavours described (as e.g. described in Valero et al (2001) *Food Chem*. 72, 51-58) it will usually also not generate off-flavour in other applications. The UHT-application is therefore a good method to evaluate the quality of lactase preparations regarding their off-flavour potential. Since proteases were held at least partly responsible for the off-flavour formation, efforts have focussed on reducing protease levels of lactase products. We have found, however, that a reduction of protease levels does not lead to complete removal of off-flavour formation in UHT-milk. We have surprisingly found that aryl-sulfatase is a crucial enzyme activity, responsible for off-flavor formation. We have found confirmative evidence by adding aryl-sulfatase to UHT-milk and which resulted in that this single enzyme is capable to mimic the off-flavour often observed in lactase-treated UHT-milk.

According to the present invention a chromatographic process is disclosed to remove the aryl-sulfatase from the lactase enzyme, which is preferably derived from *K lactis*.

We performed a detailed sensory analysis of various samples of UHT-milk that either contained no off-flavour or that contained significant levels of off-flavour (example 1). These sensory analyses were combined with detailed analysis of the chemical composition of the samples. Several compounds were identified as key aroma compounds, and most of them had been described previously as associated with UHT-milk. Surprisingly, p-cresol was also identified as a key off-flavour compound. This compounds has not been described previously among the off-flavour compounds in UHT-milk (Valero et al (2001) *Food Chem*. 72, 51-58). It can be generated by aryl-sulfatase from its sulfate conjugate that is present is very low amounts (ppb-levels) in milk (V. Lopez, R. C. Lindsay *J Agric. Food Chem*. (1993), 41, 446-454; M. Killic & R. C. Lindsay, *J Dairy Sci* (2005) 88, 7-12; M Kilic & R. C. Lindsay *J Agric Food Chem* (2005) 53, 1707-1712). We have surprisingly found that aryl-sulfatase is an enzyme activity in lactase preparations and responsible for off-flavour formation. We confirmed this by adding aryl-sulfatase to UHT milk and found that this single enzyme is indeed capable to mimic the off-flavour often observed in lactase treated UHT-milk. We subsequently developed a chromatographic process to remove the aryl-sulfatase from the lactase enzyme, which is derived from *K. lactis*. We found that the removal of arylsulfatase also results in removal of off-flavour formation in UHT-milk, as concluded from trials with taste panels. The aryl-sulfatase levels in the final lactase product are <20 units aryl-sulfatase, preferably <10 units aryl-sulfatase, even more preferably <8 units aryl-sulfatase and most preferably 0 units aryl-sulfatase. The aryl-sulfatase units are defined in example 2 and are normalized for lactase activity expressed in NLU and also defined in example 2). Several purifications routes for lactases have been described (e.g. in WO02/081673), but these purification processes were not directed to remove the aryl-sulfatase. The present results show that aryl-sulfatase and lactase, both derived from K lactis, have a very similar elution behaviour on ion exchange (Q-sepharose) and hydrophobic interaction (butyl-sepharose) chromatography. Therefore it is expected that the described prior art routes will not result in lactase preparations free from aryl-sulfatase activity.

Beside the reduction of aryl-sulfatase levels in lactase preparations by chromatography there are other ways to reduce or eliminate aryl-sulfatase activity from the lactase preparation. These are 1) the addition of sulfate to the growth medium. Sulfate is known the repress aryl-sulfatase expression (Beil et al. (1995) Eur. J. Biochem. 229, 385-394), and sulfate addition to the medium is therefore expected to lower aryl-sulfatase levels; 2) elimination or disruption of the gene for aryl-sulfatase from the genome of the organism by either random mutagenesis techniques or by a directed approach using e.g. molecular biology technologies known to the person skilled in the art, 3) screening and selection of a strain that is a natural low producer or non-producer of aryl-sulfatase activity; 4) addition of an inhibitor of the enzyme. It is e.g. known that certain classes of aryl-sulfatases are inhibited by phosphate ions.

Metabolic conjugates such as sulfates, glucuronides and phosphates are present in milk from various species, including cows milk (Lopez et al (1993) *J Agric Food Chem.* 41, 446-454; Killic et al (2005) *J Dairy Sci* 88, 7-12). Metabolic conjugation is a universally accepted means of detoxification and enhancement of aqueous solubility of foreign substances in mammals. Conjugates are most effectively formed by the liver and kidney, and they circulate in the bloodstream before elimination principally in the urine and bile. Conjugates of alkylphenols and a variety of other compounds have been found in milk from e.g. cow, goat and sheep (Lopez et al (1993) *J Agric Food Chem.* 41, 446-454). The nature and diversity of metabolic conjugates is very wide, and includes conjugates of thiophenols, phenols, o-cresol and p-cresol. The conjugation can result in the attachment of a sulphate-, phosphate or glucoronide groups. These groups can be released from the conjugate by enzymes like aryl-sulphatases, phosphates and glucoronidases, resulting in release of the toxic compound. The presence of several types of conjugates has been demonstrated in milk from cow, sheep and goat; the relative abundance of the conjugates varies between preparations and is at least partly species related (Lopez et al (1993) *J Agric Food Chem.* 41, 446-454). In cows milk, sulfate-conjugates were demonstrated to be the most abundant conjugates, but in sheep milk phosphate-conjugates are more abundant than sulfates (Lopez et al (1993) *J Agric Food Chem.* 41, 446-454).

In the present application it is demonstrated that the conjugates that are present in milk are the substrate for side activities in neutral lactase preparations. It is known that the concentration levels of these conjugates may vary for a species over time (Kilic et al, (2005) *J dairy Sci* 88, 7-12) and between species (Lopez et al (1993) *J Agric Food Chem* 41, 446-454). It is anticipated that this may affect the requirements for the lactase preparation. For instance it is anticipated that for sheep milk, in which phosphate-conjugates are very abundant, the tolerance for phosphatase-levels in lactase preparations is much lower compared to the situation where the same lactase preparation is used in cows milk which has very low levels of phosphate-conjugates. In this respect, there is no difference between preparation of intracellular lactase or extracellular lactase preparations.

In a further aspect, the invention provides a process for treating a substrate with an enzyme preparation. The enzyme preparation is preferably substantially free from aryl sulfatase.

As used herein, an enzyme preparation substantially free from arylsulfatase may encompass any enzyme preparation, in which the arylsulfatase activity is not present or present at a sufficiently low level that, upon effective dosage of the intended enzyme activity in the relevant production process, no observable decomposition of sulphated alkylphenols with the associated negative organoleptic effects as described above occurs in said production process.

As used herein, an enzyme preparation substantially free from arylsulfatase may encompass an enzyme preparation wherein the ratio of the arylsulfatase activity divided by the activity of the enzyme of interest is below a specified value. Preferred ratio's may vary depending on the enzyme and application used.

By arylsulfatase activity is meant the sulphuric ester hydrolase activity able to cleave a phenol sulfate into the phenol and sulfate moiety as described for EC 3.1.6.1. Definition for the arylsulfatase unit is provided in the Materials & Methods section (and example 2) of the present application. Definitions for the activities of the other enzymes can also be found in the Materials & Methods section of the present application.

In a further aspect of the invention, the invention provides an enzyme preparation comprising a carboxypeptidase, which enzyme preparation comprises less than 10000 units (ASU) of aryl sulfatase activity per unit of carboxypeptidase (CPG). Preferably, the enzyme preparation comprises less than 5000 units, more preferably less than 1000 units, more preferably less than 500 units, more preferably less than 100 units, more preferably less than 50 units, more preferably less than 10 units of arylsulfatase activity per carboxypeptidase unit (CPG).

In a further aspect, the invention provides an enzyme preparation comprising a proline-specific protease, which enzyme preparation comprises less than 300*10E3 units (ASU) of arylsulfatase activity per unit of prolin protease (PPU). Preferably, the enzyme preparation comprises less than 100*10E3 units, preferably less than 50*10E3 units, preferably less than 10*0E3 units, preferably less than 5000 units of arylsulfatase per protease unit (PPU).

In a further aspect, the invention provides an enzyme preparation comprising a (neutral) lactase, which enzyme preparation comprises less than 40 units (ASU) arylsulfatase activity per NLU of lactase activity. Preferably, the enzyme preparation comprises less than 30 units arylsulfatase activity per NLU of lactase activity, more preferably less than 20 units arylsulfatase activity per NLU of lactase activity and most preferably less than 10 units arylsulfatase activity per NLU of lactase activity.

In a further aspect, the invention provides an enzyme preparation comprising an (acid) lactase, which enzyme preparation comprises less than 400 units (ASU) of arylsulfatase activity per ALU of lactase activity. Preferably, the enzyme preparation comprises less than 100 units (ASU) of arylsulfatase activity, preferably 30 units arylsulfatase activity per ALU of lactase activity, more preferably less than 20 units arylsulfatase activity per ALU of lactase activity and most preferably less than 10 units arylsulfatase activity per ALU of lactase activity.

In a further aspect, the invention provides an enzyme preparation comprising an aminopeptidase, which enzyme preparation comprises less than 1000 units (ASU) of aryl sulfatase activity per APU, preferably less than 300 units (ASU) of aryl sulfatase activity per APU, preferably less than 100 units (ASU) of aryl sulfatase activity per APU, preferably less than 30 units (ASU) of aryl sulfatase activity per APU, preferably less than 10 units (ASU) of aryl sulfatase activity per APU.

In a further aspect, the invention provides an enzyme preparation comprising an esterase and/or a lipase, which enzyme preparation comprises less than 10*10E6 units (ASU) of aryl sulfatase activity per BGE, preferably less than 3*10E6 units (ASU) of aryl sulfatase activity per BGE, preferably less than 1*10E6 units (ASU) of aryl sulfatase activity per BGE, preferably less than 300*10E3 units (ASU) of aryl sulfatase activity per BGE.

Treatment of a substrate with an enzyme preparation substantially free from arylsulfatase may also encompass the treatment of a substrate wherein the level of arylsulfatase in the substrate during said treating is below a specified value.

In a further aspect, the invention provides a process for treating a substrate with an enzyme preparation, wherein the level of arylsulfatase in the substrate during said treating is at most 500*10E3 arylsulfatase units per liter of substrate, preferably at most 250*10E3, preferably at most 100*10E3, preferably at most 50*10E3, preferably at most 25*10E3 arylsulfatase units per liter of substrate. Maintaining the level of arylsulfatase below the abovementioned values was found to be particular advantageous when the substrate is milk, preferably cow milk.

An enzyme preparation substantially free from aryl sulfatase may also encompass any enzyme preparation obtained by purifying a crude enzyme preparation which contains an enzyme of interest and arylsulfatase, wherein arylsulfatase is separated from the enzyme of interest.

Accordingly, the invention also provides a process for preparing an enzyme preparation, which process comprises purifying a crude enzyme preparation which contains an enzyme of interest and arylsulfatase, wherein arylsulfatase is separated from the enzyme of interest. The process may advantageously comprise treating a substrate with the purified enzyme preparation.

The purification step has the effect that the activity of arylsulfatase relative to the activity of enzyme of interest is reduced. Preferably, the purifying results in a reduction of arylsulfatase activity of at least 50%, preferably at least 80%, more preferably at least 90%, more preferably at least 95%, more preferably at least 99%. The skilled person will appreciate that this is understood to mean that preferably $(a_{AS,pur}/a_{enz,pur})/(a_{AS,crude}/a_{enz,crude}) \leq 0.5$, preferably $\leq 0.2$, preferably $\leq 0.1$, preferably $\leq 0.05$, preferably $\leq 0.01$, wherein $a_{AS,pur}$=arylsulfatase activity in purified enzyme preparation (unit/ml)

$a_{enz,pur}$=activity of enzyme of interest in purified enzyme preparation (unit/ml)

$a_{AS,crude}$=aryl sulfatase activity in crude enzyme preparation (unit/ml)

$a_{enz,crude}$=activity of enzyme of interest in crude enzyme preparation (unit/ml)

The purification can be effected in any suitable manner. In a preferred embodiment, the purifying is by chromatography. Processes for purifying enzyme preparations using chromatography are known per se. Selecting the most appropriate chromatographic separation methods depend on molecular characteristics of both the relevant enzyme and of the relevant arylsulfatase activity present. Relevant molecular characteristics are the isoelectric point, hydrophobicity, molecular surface charge distribution, molecular weight of the relevant enzyme and the side activity as well as several other protein chemical properties. A practical background on the use of these characteristics in selecting the appropriate chromatographic separation process, can be found in a.o. the Protein Purification Handbook (issued by Amersham Pharmacia Biotech, nowadays GE Healthcare Bio-Sciences, Diegem, Belgium). Suitable chromatrographic separation methods comprise ion exchange chromatography, affinity chromatography, size exclusion chromatography, hydrophobic interaction chromatography and others. For the present invention ion exchange chromatography or hydrophobic interaction chromatography are preferred.

In a preferred embodiment, the purification is performed in a single chromatographic separation step. The fact that enzymatic activity can be efficiently separated from the contaminating arylsulphatase activity in a single chromatographic step, is particularly advantageous for the industrial applicability of the process according to the invention.

The enzyme preparation may comprise any suitable enzyme. In a preferred embodiment, the enzyme, hereinafter also referred to as enzyme of interest, is a lactase, a protease, a lipase, or an esterase. Enzymes that may be used according to the invention are disclosed hereinafter.

The internationally recognized schemes for the classification and nomenclature of all enzymes are provided by IUMB. An updated IUMB text for EC numbers can be found at the internet site: http://www.chem.qmw/ac.uk/iubmb/enzyme/EC3/4/11/. In this system enzymes are defined by the fact that they catalyze a single reaction. This implies that several different proteins are all described as the same enzyme, and a protein that catalyses more than one reaction is treated as more than one enzyme.

According to the system, proteases can be subdivided into endo- and exoproteases. Moreover, socalled di- and tripeptidyl peptidases exist. Endoproteases are those enzymes that hydrolyze internal peptide bonds, exoproteases hydrolyze peptide bonds adjacent to a terminal α-amino group ("aminopeptidases"), or a peptide bond between the terminal carboxyl group and the penultimate amino acid ("carboxypeptidases"). The endoproteases are divided into sub-subclasses on the basis of catalytic mechanism. There are sub-subclasses of serine endoproteases (EC 3.4.21), cysteine endoproteases (EC 3.4.22), aspartic endoproteases (EC 3.4.23), metalloendoproteases (EC 3.4.24) and threonine endoproteases (EC 3.4.25). Proteases typically to clot milk for cheese production, such as chymosin (EC 3.4.23.4) or mucorpepsin (EC 3.4.23.23), all belong to the class of the aspartic endoproteases.

Among the exoproteases, the so-called aminopeptidases (EC 3.4.11) can sequentially remove single amino-terminal amino acids from protein and peptide substrates. Among the exoproteases, the carboxypeptidases (EC 3.4.16, 3.4.17 and 3.4.18) can sequentially remove single carboxy-terminal amino acids from protein and peptide substrates. Di- and tripeptidyl peptidases (EC 3.4.13, 3.4.14 and 3.4.15) can cleave off dipeptides or tripeptides from either the amino- or the carboxyterminal side of peptides or proteins.

In an embodiment of the invention, the enzyme is a protease with the exclusion of an aspartic endoprotease (EC3.4.23).

Other enzymes acting on proteins or peptides and of particular relevance within the scope of the present application, are the omega peptidases (EC 3.4.19) and enzymes able to transform side groups of amino acids. The substrate for such transformation reactions can be free amino acids or protein- or peptide-bound amino acids. Examples of the latter group of enzymes are enzymes that can selectively hydrolyse gamma amide groups of protein bound glutamines, i.e. the peptide-glutaminases (EC 3.5.1.43 and 3.5.1.44).

Furthermore enzymes able to crosslink proteins or peptides such as transglutaminase (EC 2.3.2.13) and protein-lysine 6-oxidase (EC 1.4.3.13) represent typical examples.

Lactase (EC 3.2.1.23), a microbial beta-galactosidase able to decompose the lactose, is of particular relevance within the scope of the present application.

Lipases and esterases are of particular relevance within the scope of the present application because these enzymes are commonly used in the production of EMC's (Enzyme Modified Cheeses) and enjoy an increasing interest for accelerating cheese aging. Therefore, lipases and esterases are prime candidates to be purified according to the process of the current invention. According to the IUMB system lipases and esterases belong to the carboxylic ester hydrolases (EC 3.1.1). Whereas esterases can act on a broad variety of substrates, lipases (EC 3.1.1.3) cleave triacylglycerols only. Lipases capable of removing formate, acetate, propionate or butyrate from triacylglycerols are sometimes also referred to as "esterases". In the present application the term "esterase" refers to enzymes that can efficiently remove such short chain carboxylic acids from triacylglycerols. The recovery of amphiphilic enzymes such as lipases or esterases is optionally improved by using bile acids or another food grade emulsifier. Methods for the activity determination of lipases and esterases are provided in the Materials & Methods section.

Industrially available, food grade enzyme preparations are typically obtained from mammalian tissue, e.g. trypsin from pancreas, or from plant material, e.g. papain from papaya fruits. In a preferred embodiment the enzyme is obtained from a microbial strain, for instance bacteria, e.g. *Bacillus* species, or yeasts, e.g. *Saccharomyces, Kluyveromyces* or *Pichia*, or filamentous fungi. Filamentous fungi known to produce food grade enzyme preparations are for instance *Aspergillus, Rhizomucor, Rhizopus, Trichoderma* and *Talaromyces*. In an embodiment of the invention, the enzyme preparation is produced by or derived from a filamentous fungus, for instance *Aspergillus niger* or *Aspergillus oryzae*. As used herein such enzyme preparations also encompass self-cloned enzyme preparations produced by either *A. niger* or by *A. oryzae*.

The enzyme of interest may be produced by microbial fermentation processes using fungi that produce and preferably secrete the protease of interest in the fermentation broth. In the art, such fermentation processes are known, see for example WO 02/45524. In the processes of the prior art, the enzyme may be recovered from the fermentation broth by techniques also known in the art. As a first step, the cells of the production organism may be separated from the broth by centrifugation or filtration. The cell free broth may be concentrated, for example by ultrafiltration, and subsequently chromatographically purified. Fungal strains typically produce more than one arylsulphatase activity so that the chromatographic separation of the relevant enzyme from these arylsulfatase activities in a single step, is not trivial. An additional complication is that the different enzyme activities secreted by a specific microorganism, i.e. the enzyme activity sought as well as the various arylsulphatase activities, have isoelectric points closely together. Upon chromatographic separation of the desired enzymatic activity and the contaminating arylsulfatase activities, the purified enzyme preparation thus obtained may be stabilized.

In case the enzyme is not secreted by the microorganism but remains intracellular, the production organism may be recovered by filtration or centrifugation after which the retained cells may be lysed to release the relevant enzymatic activity. After another filtration or centrifugation step to remove the cell debris, the liquid fraction may be concentrated and stabilized as described above for the secreted enzyme.

The purified and liquid enzyme preparations may be concentrated and mixed with known stabilizers such as glycerol or other polyols. Alternatively, solid preparations may be obtained from concentrated enzyme solutions by known precipitation and/or evaporation steps followed by well known (spray) drying techniques.

According to the invention a substrate may be treated with the enzyme preparation. The substrate may be any suitable substrate. Preferably, the substrate is a proteinaceous substrate. The proteinaceous substrate may be any substrate comprising protein. In a preferred embodiment, the substrate contains milk protein, for instance casein and/or whey protein. Examples of preferred substrates are milk, milk-derived products, fermented milk products (for instance yoghurt) whey and/or hydrolysates. The substrate may also comprise meat.

As a hydrolysate may be used any product that is formed by the enzymatic hydrolysis of a proteinaceous substrate protein, preferably an animal derived substrate protein. Whey protein hydrolysates, casein hydrolysates and skim milk hydrolysates are preferred.

In a preferred embodiment, the substrate contains an alkyl phenol substituted with a sulfate group. By alkylphenol is meant a phenol group of which at least one aromatic proton has been replaced by an alkyl group. The length of the alkyl group may vary and may be branched or substituted. Preferred alkylphenols are methyl and ethyl phenols.

By a sulphated alkylphenol is meant an alkylphenol which is conjugated at the hydroxyl group by sulfation.

Arylsulphatase (EC 3.1.6.1) is a sulphuric ester hydrolase able to cleave an alkyl phenol sulfate into the alkyl phenol and sulfate moiety.

The treatment of the substrate may involve any process wherein a substrate is contacted with the enzyme preparation. The treatment may involve any process wherein the substrate is incubated in the presence of the enzyme preparation. The enzyme preparation may be added to the substrate in any suitable manner.

The process may be any process wherein a product is produced, for instance a nutritive product, preferably a dairy product. As used herein, a dairy product encompasses any composition that contains milk protein, for instance casein and/or whey protein. Examples are milk, milk-derived products, fermented milk products (e.g. yoghurt), condensed milk, evaporated milk, dry milk, frozen milk, ice cream, whey; and/or cheese. The product may also be a hydrolysate.

The enzyme preparation may be used to prepare any suitable product, for instance a nutritive product, preferably a dairy product.

The invention also relates to the use of the enzyme preparation according to the invention to prevent or reduce the development of off-flavor.

In an aspect, the invention provides a process to produce a host cell which is an arylsulfatase deficient strain, which comprises bringing a culture which produces arylsulfatase under conditions that part of the culture is modified to form the host cell which is arylsulfatase deficient and isolating the host cell.

In a preferred embodiment mutagenesis conditions are used, preferably random mutagenesis conditions such as physical or chemical mutagenesis.

In a preferred embodiment, recombinant genetic manupilation techniques are used, preferably one-step gene disruption, marker insertion, site directed mutagenesis, deletion, RNA interference, anti-sense RNA.

The invention further provides a process to produce a polypeptide by a method comprising:
(a) cultivating an arylsulfatase deficient host cell in a nutrient medium, under conditions conductive to expression of the polypeptide
(b) expressing the polypeptide in said host cell, and
(c) optionally recovering the polypeptide from the nutrient medium or from the host cell.

The invention further provides a process to produce a polypeptide by a method comprising:
(a) transforming an arylsulfatase deficient host cell with an expression vector, wherein the vector expresses the polypeptide,
(b) cultivating the host cell in a nutrient medium, under conditions conductive to expression of the polypeptide
(c) expressing the polypeptide in the host cell, and
(d) optionally recovering the polypeptide from the nutrient medium or from the host cell.

The invention further provides a process to produce a polypeptide by a method comprising:
(a) cultivating a host cell in a nutrient medium that prohibits the production of arylsulfatase and under conditions conductive to expression of the polypeptide
(b) expressing the polypeptide in said host cell, and
(c) optionally recovering the polypeptide from the nutrient medium or from the host cell.

The invention further provides a process to produce a polypeptide by a method comprising:
(a) transforming a host cell with an expression vector, wherein the vector expresses the polypeptide,
(b) cultivating the host cell in a nutrient medium that prohibits the production of arylsulfatase and under conditions conductive to expression of the polypeptide
(c) expressing the polypeptide in the host cell, and
(d) optionally recovering the polypeptide from the nutrient medium or from the host cell.

In a preferred embodiment, the polypeptide is an enzyme. In a preferred embodiment, a process for preparing an enzyme preparation is provided, said process comprising preparing an enzyme by a process as disclosed herein, and recovering an enzyme preparation from the nutrient medium or from the host cell.

Further disclosure is given below.

Fermentative Repression

In a preferred embodiment, the enzyme preparation may be produced using an industrial host strain that is cultivated in a growth medium that limits or prohibits the production of arylsulfatases. For Pseudomonas aeruginosa it has been described that after cultivation in a medium containing an excess of sulphate as sole sulphur source, no significant level of arylsulfatase could be detected, while the use of ethanesulfonate as sole sulphur source leads to the production of significant amounts of arylsulfatase activity (Beil et al. (1995) Eur. J. Biochem. 229, 385-394). Therefore, it is conceivable that using an excess of sulphate in the fermentation medium also has a repressing effect on the production of arylsulfatase activity in industrially more important micro-organisms. Growth of the enzyme production organism in a medium containing an excess of sulphate as sulphur source might therefore lead to the production of preferable enzyme products with a reduced amount of arylsulfatase activity. With an excess of sulphate in the medium it is meant here that a significant amount of free sulphate is still left in the broth after growth of the micro-organism has been completed. It is not required for this invention that sulphate is the sole sulphur source in the growth medium, as long as the molar amount of sulphate in the growth medium is higher than the molar amount of any other sulphur containing substance, during the complete growth period. Additionally, also cysteine or thiocyanate might be used instead of sulphate, as preferred sulphur source in the repression of arylsulfatase activity. Additionally, it is also relevant to have a significant amount of sulphate, or another repressing sulphur source, in all solutions during washing, storage and other down-stream-processing steps, to prevent the derepression of arylsulfatase activity in the broth, even after the end of the fermentation.

Classical Strain Improvement

An arylsulfatase deficient strain may be obtained by genetic engineering using recombinant genetic manipulation techniques, submitting the host to mutagenesis, or both. Modification or inactivation of the genes coding for arylsulfatase of the present invention may result from subjecting the parent cell to mutagenesis and selecting for mutant cells in which the ability to express arylsulfatases has been reduced by comparison to the parental cell. The mutagenesis, which may be specific or random, may be performed, for example, by use of a suitable physical or chemical mutagenizing agent, by use of a suitable oligonucleotide, or by subjecting the DNA sequence to PCR-generated mutagenesis. Furthermore, the mutagenesis may be performed by use of any combination of these mutagenizing agents.

Examples of a physical or chemical mutagenizing agent suitable for the present purpose include gamma or ultraviolet (UV) radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogs. When such agents are used, the mutagenesis is typically performed by incubating the parent cell to be mutagenized in the presence of the mutagenizing agent of choice under suitable conditions, and selecting for mutant cells exhibiting reduced expression of the gene. Alternatively, such strains may be isolated using genetic techniques such as hybridization or mating, and protoplast fusion or any other classical genetic technique to induce genetic diversity. The arylsulfatase deficient strain obtained may be subsequently selected by monitoring the expression level of the arylsulfatase. Optionally, the arylsulfatase deficient strain is subsequently selected by measuring the expression level of a given gene of interest to be expressed in the host cell. Selection of strains having reduced arylsulfatase activity may be done by directly measuring arylsulfatase activity in culture broth, in culture supernatant, in permeabilized cells, or in cell lysate. For measuring arylsulfatase activity it is possible to optionally permeabilize cells of the industrial production strain, incubate with a fluorescent substrate (such as 4-methylumbelliferone-sulphate (MUS)), until the substrate has been taken up by the cells, and screen for cells with lower arylsulfatase activity by measuring the decrease in fluorescence. Such measurement may be done directly using a conventional fluorimeter in individual cultures, or preferably be done by flow cytometry in such a way that the cells with low fluorescence can be sorted out and used for further cultivation. Cells used in such a procedure may or may not be mutagenized prior to the incubation with fluorescent substrate.

Alternatively, strains having reduced arylsulfatase activity may be isolated by selection for strains that are not able to grow on sulphate esters of alkylesters (such as cresyl sulphate or ethanesulfonate) as sole sulphur source in the growth medium.

Isolation of suitable strains according to the invention may require several rounds of classical genetic techniques to be applied, especially in industrial production strains that are not haploid, but diploid, aneuploid or have a different ploidy such is the case with many industrial yeast strains, or in case the industrial production strain contains multiple genes coding for arylsulfatase, such is the case in fungi.

Recombinant DNA Techniques

Alternatively, industrial production strains that have a reduced amount of arylsulfatase activity may be constructed using recombinant DNA technology. Several techniques for gene inactivation or gene disruption are described in the art, such as one-step gene disruption, marker insertion, site directed mutagenesis, deletion, RNA interference, anti-sense RNA, and others, and may all be used to lower, inhibit or disturb the synthesis of the arylsulfatase activity in order to obtain a industrial production strain with decreased arylsulfatase activity. Also the inactivation of arylsulfatase by altering the control sequence(s) directing the expression of the arylsulfatase gene are part of the present invention. An example thereof is the lowering of the promoter activity by gene disruption.

Using modern genetic modification techniques, one can obtain a recombinant arylsulfatase deficient strain, preferably by disturbing a gene coding for arylsulfatase activity, more preferably by inserting a marker gene into a gene coding for arylsulfatase activity, most preferably by removal of part or all of the arylsulfatase coding region from the genome. Methods to perform such gene inactivations have been described for many different micro-organisms and are known to those skilled in the art (see i.e. EP357127) and is also described in Example 8. Expression of arylsulfatases in the mutant cell may thereby be reduced or eliminated. Dependent on the host strain that is modified using these techniques, the procedure should be repeated several times to remove all or most of the arylsullfatase coding sequences.

Modification or inactivation of a host gene such as arylsulfatase may be performed by established antisense techniques using a nucleotide sequence complementary to the nucleotide sequence of the gene. More specifically, expression of the gene may be reduced or eliminated by introducing a nucleotide sequence complementary to the nucleotide sequence, which may be transcribed in the cell and is capable of hybridizing to the mRNA produced in the cell. Under conditions allowing the complementary antisense nucleotide sequence to hybridize to the mRNA, the amount of protein translated is thus reduced or eliminated. Examples of expressing an anti-sense RNA is provided by Ngiam et al. (*Appl. Environ. Microbiol.* 66:775-782, 2000) and Zrenner et al. (*Planta* 190:247-252, 1993).

Modification, downregulation, or inactivation of a host gene may be obtained via RNA interference (RNAi) techniques (*FEMS Microb. Lett.* 237:317-324, 2004). More specifically, expression of the gene by a filamentous fungal cell may be reduced or eliminated by cloning identical sense and antisense portions of the nucleotide sequence, which expression is to be affected, behind each other with a nucleotide spacer in between, inserting into an expression vector, and introducing the expression vector into the cell where double-stranded RNA (dsRNA) may be transcribed and then processed to shorter siRNA that is able to hybridize to target mRNA. After dsRNA is transcribed, formation of small (21-23) nucleotide siRNA fragments will lead to a targeted degradation of the mRNA, which is to be affected. The elimination of the specific mRNA can be to various extents. The RNA interference techniques described in WO 2005/05672 and WO 2005/026356 may be used for modification, downregulation, or inactivation of the host gene.

The arylsulfatase deficient strain, which has been modified or inactivated by any of the methods described above and produces fewer arylsulfatase activity than the parent cell when cultured under identical conditions as measured using the same assays as defined before, may harbor another nucleotide sequence.

Such industrial production strains with decreased arylsulfatase activity isolated or constructed by classical genetic techniques or recombinant DNA technology may be used for relevant industrial processes that require the final product to lack off-flavour. Preferably these strains are used for the production of industrially relevant enzymes. More preferably these strains are used for the production of enzymes that are used in the food industry, even more preferably these enzymes are used in processing of dairy products. Most preferably such industrial production strains with decreased arylsulfatase activity are used for the production of lactase.

Host Strains

Suitable industrial host strains are preferably prokaryotic microorganisms such as bacteria, or more preferably eukaryotic organisms, for example fungi, such as yeasts or filamentous fungi, or plant cells. Bacteria from the genus *Bacillus* are very suitable as hosts because of their capability to secrete proteins into the culture medium. Other bacteria suitable as hosts are those from the genera *Streptomyces* and *Pseudomonas*. A preferred yeast host cell for the expression of a DNA sequence encoding the enzyme of interest is one of the genus *Saccharomyces, Kluyveromyces, Hansenula, Pichia, Yarrowia,* or *Schizosaccharomyces*. More preferably, a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica,* and *Schizosaccharomyces pombe*.

Most preferred for the expression of an enzyme are, however, filamentous fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia,* and *Talaromyces*. More preferably a filamentous fungal host cell is of the species *Aspergillus oryzae, Aspergillus sojae* or *Aspergillus nidulans* or is of a species from the *Aspergillus niger* Group (as defined by Raper and Fennell, The Genus *Aspergillus*, The Williams & Wilkins Company, Baltimore, pp 293-344, 1965). These include but are not limited to *Aspergillus niger, Aspergillus awamori, Aspergillus tubigensis, Aspergillus aculeatus, Aspergillus foetidus, Aspergillus nidulans, Aspergillus japonicus, Aspergillus oryzae* and *Aspergillus ficuum*, and also those of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosphorum* and *Thielavia terrestris*.

Examples of preferred industrial production strains within the scope of the present invention are fungi such as *Aspergillus* species (in particular those described in EP-A-184,438 and EP-A-284,603) and *Trichoderma* species; bacteria such as *Bacillus* species (in particular those described in EP-A-134,048 and EP-A-253,455), especially *Bacillus subtilis*, *Bacillus licheniformis*, *Bacillus amyloliquefaciens*, *Pseudomonas* species; and yeasts such as *Kluyveromyces* species (in particular those described in EP-A-096,430 such as *Kluyveromyces lactis* and in EP-A-301,670) *Saccharomyces* species, such as *Saccharomyces cerevisiae*, or *Pichia pastoris, Hansenula polymorpha, Candida utilis* or *Yarrowia lipolytica*. The current invention most preferably relates to the production of lactase lacking arylsulfatase activity by *Kluyveromyces lactis*.

Arylsulfatase deficient strains suitable for the production of a given polypeptide or enzyme in an industrial setting have been isolated, wherein surprisingly the arylsulfatase deficient strain produce at least the same amount of polypeptide or enzyme as the wild type strain they originate from under the same culture conditions.

Preferably, the arylsulfatase deficient strains of the invention are strains have less than 50% of the detectable intracellular or extracellular arylsulfatase activity as detected in a model reaction (see experimental information in the Example 2). More preferably, the arylsulfatase deficient strains of the invention are strains having less than 50% of the intracellular arylsulfatase activity. More preferably, the arylsulfatase deficient strains of the invention are strains having an intracellular arylsulfatase activity, which is less than 25% of the intracellular arylsulfatase activity of the wild type strain they originate from as detected in a model reaction, preferably less than 10%, more preferably less than 5%, more preferably less than 1% and most preferably the arylsulfatase activity is undetectable in the arylsulfatase deficient strains.

In this application, *K. lactis* strain CBS 2359 is taken as a reference of wild type arylsulfatase levels obtainable in an *K. lactis* culture, as a reference of wild type polypeptide level obtainable in an *K. lactis* culture and as a reference of intracellular arylsulfatase activity obtainable in an *K. lactis* culture. Arylsulfatase deficient *K. lactis* strains are defined as strains that produce less arylsulfatase activity than the *K. lactis* strain CBS 2359 under the same culture conditions. Preferably, the arylsulfatase deficient strain is a *K. lactis* strains having less than 50% of the intracellular arylsulfatase activity of the *K. lactis* CBS 2359 strain as detected in a model reaction. More preferably, the arylsulfatase deficient *K. lactis* strains of the invention are strains having an intracellular arylsulfatase activity, which is less than 25% of the intracellular arylsulfatase activity of the *K. lactis* CBS 2359 strain they originate from as detected in a model reaction, preferably less than 10%, more preferably less than 5%, more preferably less than 1% and most preferably the arylsulfatase activity is undetectable in the arylsulfatase deficient *K. lactis* strains. According to a preferred embodiment of the invention, the arylsulfatase deficient *K. lactis* strain used has been obtained by applying the method defined later in this application.

A large variety of systems for detection of polypeptide are known to the skilled person. Detection systems include any possible assay for detection of polypeptide or enzymatic activity. By way of example these assay systems include but are not limited to assays based on colorimetric, photometric, fluorometric, turbidimetric, viscosimetric, immunological, biological, chromatographic, and other available assays.

Preferably, if the polypeptide produced is an enzyme, the amount of active enzyme produced is determined by measurement of its activity in a model reaction (see example 2).

According to a further preferred embodiment, the arylsulfatase deficient strain of the invention is characterized by the fact that when this strain has been transformed with an expression construct comprising a gene coding for a polypeptide, said strain produces at least the amount of the polypeptide the wild type strain it originates from would produce under the same culture conditions, when the wild type strain has also been transformed with the same expression construct as the arylsulfatase deficient strain. Preferably, the arylsulfatase deficient strains of the invention are strains that produce the same amount or more of a given polypeptide than the wild type strain they originate from under the same culture conditions. More preferably, the arylsulfatase deficient strain produces more of a given polypeptide than the wild type strain they originate from under the same culture conditions.

Production of Other Native or Heterologous Polypeptides and Other Sequences

According to yet another embodiment, the present invention relates to methods of transcribing a nucleotide sequence in a host cell, wherein the transcribed sequence encodes a desired polypeptide or is a functional nucleic acid molecule, comprising:
(a) cultivating, in a nutrient medium, a host cell comprising (i) a promoter, (iv) a downstream nucleotide sequence which encodes a polypeptide, (iii) a translational stop signal and (iv) a transcriptional stop signal,
(b) expressing the polypeptide in the host cell, and
(c) optionally, recovering the polypeptide from the nutrient medium or from the host cell.

The polypeptide produced may be sensitive to protease degradation. In this case, a mutant host cell which is protease deficient will be used. The arylsulfatase deficient strain is preferably produced according to the method of the present invention. The arylsulfatase deficient strain may be grown or maintained in a nutrient medium suitable for production of the desired polypeptide using methods known in the art. For example, cells may be plated on a solid substrate, shaken in a flask, cultivated in small-scale or large-scale fermentation (including continuous, batch, fedbatch, or solid-state fermentation) in laboratory or industrial fermentors in a suitable medium and under conditions allowing the polypeptide to be expressed and/or isolated. Cultivation takes place in a suitable nutrient medium comprising carbon and nitrogen sources and inorganic salts, using procedures known in the art (see, e.g., Bennett & LaSure, eds., *More Gene Manipulations in Fungi*, Academic Press, Calif., 1991). Suitable media are available from commercial suppliers or may be prepared using published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, or size exclusion), electrophoresis (e.g., preparative isoelectric focusing), differential solubility (e.g., acetone or ammonium sulfate precipitation), or extraction (e.g., chaotrope, salt, or pH). See, e.g., Janson & Ryden, eds., *Protein Purification*, VCH Publishers, New York, 1989.

The polypeptide may be detected using methods known in the art that are specific for the polypeptide. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

The polypeptide may be any polypeptide whether native or heterologous to the arylsulfatase deficient strain. The term "heterologous polypeptide" is defined herein as a polypeptide, which is not produced by a wild-type strain. The term "polypeptide" is not meant herein to refer to a specific length of the encoded produce and therefore encompasses peptides, oligopeptides and proteins. The nucleotide sequence encoding a heterologous polypeptide may be obtained from any prokaryote, eukaryote, or other source and may be a synthetic gene. The term "obtained from" as used herein in connection with a given source shall mean that the polypeptide is produced by the source or by a cell in which a gene from the source has been inserted.

The desired polypeptide may be an antibody or antigen-binding portion thereof, antigen, clotting factor, enzyme, peptide hormone or variant thereof, receptor or ligand-binding portion thereof, regulatory protein, structural protein, reporter, transport protein, intracellular protein, protein involved in a secretory process, protein involved in a folding process, chaperone, peptide amino acid transporter, glycosylation factor, or transcription factor. The polypeptide may be secreted extracellularly into culture medium.

There is no limitation to a specific enzyme. Preferred enzymes are disclosed in the remainder of the specification and examples.

Alternatively the polypeptide may be an intracellular protein or enzyme such as, for example, a chaperone, protease, or transcription factor. An example of this is described by Punt et al. (*Appl. Microbiol. Biotechnol.* 50:447-454, 1998). This can be used for example to improve the efficiency of a host cell as protein producer if this polypeptide, such as a chaperone, protease, or transcription factor, is known to be a limiting factor in protein production.

In the methods of the present invention, the arylsulfatase deficient strain may also be used for the recombinant production of polypeptides, which are native to the cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of polypeptides native to the cell, to the extent that such expression involves the use of genetic elements not endogenous to the cell, or use of endogenous sequence elements which have been manipulated to function in a manner that do not normally occur in the filamentous fungal cell. The techniques used to isolate or clone a nucleotide sequence encoding a heterologous polypeptide are known in the art and include isolation from genomic DNA, preparation from cDNA, or a combination thereof.

In the methods of the present invention, heterologous polypeptides may also include a fused or hybrid polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant fungal cell. An isolated nucleotide sequence encoding a heterologous polypeptide of interest may be manipulated in a variety of ways to provide for expression of the polypeptide. Expression will be understood to include any step involved in the production of the polypeptide including, but not limited to, transcription, posttranscriptional modification, translation, posttranslational modification, and secretion. Manipulation of the nucleotide sequence encoding a polypeptide prior to its insertion into a vector may be desirable or necessary depending on the expression vector. The techniques for modifying nucleotide sequences utilizing cloning methods are well known in the art.

The DNA sequence encoding the polypeptide to be produced may be operably linked to appropriate DNA regulatory regions to ensure a high level of expression of said DNA sequence and preferably a high secretion level of said polypeptide. If the polypeptide to be produced is native to the arylsulfatase deficient strain, its native secretion signal is preferably used. Alternatively, if the polypeptide to be produced is not native to the arylsulfatase deficient strain, a fusion construct is preferably made comprising i.e. the glucoamylase gene of *Aspergillus niger* fused to the heterologous gene to be produced. According to a preferred embodiment of the invention, the regulatory regions of the *Aspergillus oryzae* alpha amylase gene are used. According to a more preferred embodiment of the invention, the regulatory regions of the *A. niger* glucoamylase gene are used. According to a more preferred embodiment of the invention, the regulatory regions of the *K. lactis* lactase gene are used. The DNA construct may also comprise a selectable marker. Alternatively, the selectable marker may be present on a second DNA construct. By way of example these markers include but are not limited to amdS (acetamidase genes), auxotrophic marker genes such as argB, trpC, or pyrG and antibiotic resistance genes providing resistance against e.g. phleomycin, hygromycin B or G418. Preferably, the marker gene is the acetamidase gene from *Aspergillus nidulans*. More preferably, the acetamidase gene from *Aspergillus nidulans* is fused to the gpdA promoter. More preferably, the acetamidase gene from *Aspergillus nidulans* is fused to the *Saccharomyces cerevisiae* ADH1 promoter.

A method was developed for obtaining arylsulfatase deficient strain which are suitable for producing high yields of a polypeptide and which can be used as polypeptide producers in an industrial setting. The polypeptide may be homologous or heterologous for said arylsulfatase deficient strain. In case of a heterologous polypeptide or enzyme, the wild type strain on which the method of the invention is applied may have been earlier transformed to express a gene coding for such polypeptide or enzyme as has been described earlier in the description. Such arylsulfatase deficient strains produce at least the amount of polypeptide the wild type strains they originate from produce under the same culture conditions. Alternatively, the construction of the arylsulfatase deficient strain can be performed prior to the transformation with a gene coding for such polypeptide or enzyme as has been described earlier in the description.

According to an embodiment of the invention, polypeptides are consequently produced in a host cell of the present invention with a reduced arylsulfatase phenotype, which cell is a mutant of a parent cell useful for the production of enzymes useful in the food industry, in which the parent cell comprises one or more nucleotide sequences encoding arylsulfatases and the mutant cell produces less arylsulfatase activity than the parent cell when cultured under the same conditions.

Preferred features disclosed for one aspect of the invention are also applicable to other aspects of the invention.

The invention will now be elucidated with reference to the following examples without however being limited thereto.

MATERIALS & METHODS

Figure 1:
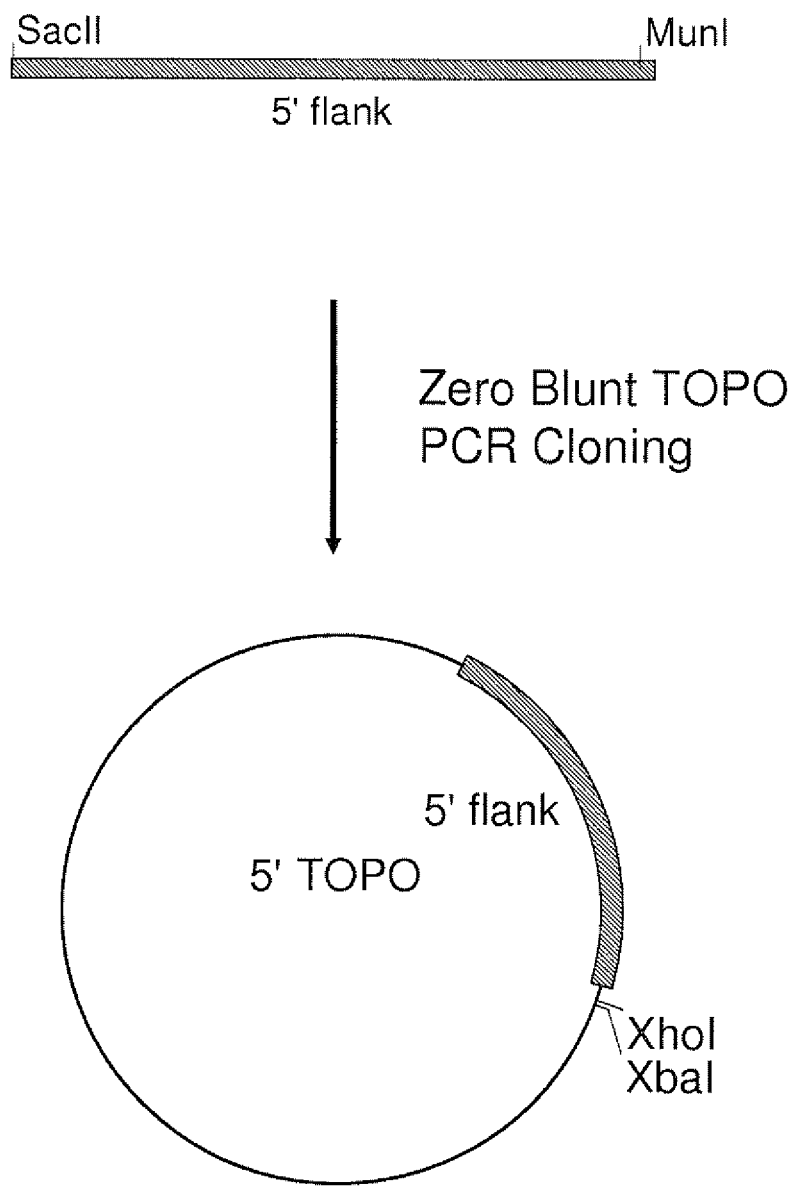
FIG. 1: Cloning of the 5'-flank of the *K. lactis* arylsulfatase gene in TOPO vector
Figure 2:
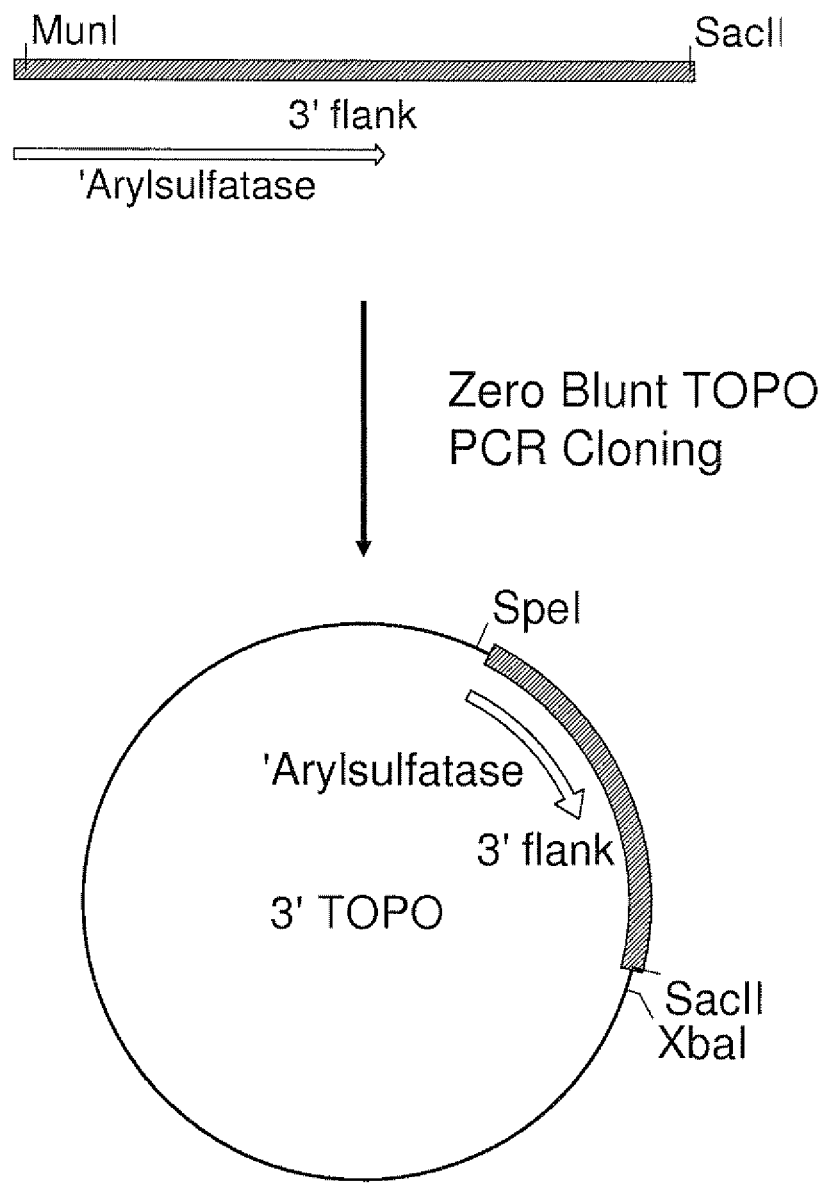
FIG. 2: Cloning of the 3'-flank of the *K. lactis* arylsulfatase gene in TOPO vector

Activity Assay Arylsulfatase:

Arylsulfatase activity was determined using p-nitrophenylsulfate (obtained from Sigma) as a substrate. For activity measurements, 0.5 ml of substrate solution (20 mM p-nitrophenylsulfate in 100 mM $NaP_i$ buffer pH6.5) was mixed with 0.5 ml sample solution containing the arylsulfatase activity. The solution was incubate at 37° C. for 3 hours. Than the reaction was stopped by addition of 1.5 ml 0.5M NaOH. The OD at 410 nm was determined (1 cm pathlength) against a blank experiment in which water was added instead of sample solution. As reference, a solution was prepared in which the enzyme was added after the reaction was stopped with NaOH. The $OD_{410}$ of this reference solution was subtracted from the $OD_{410}$ determined for the solution in which the enzyme was active for three hours. An aryl sulfatase unit (ASU) is expressed as the change in $OD_{410}*10E6/hr$. For liquid products, the aryl sulfatase activity can expressed as the change in $OD_{410}*10E6/hr$ per ml of product. For solid products, the aryl sulfatase activity can expresses as the change in $OD_{410}*10E6/hr$ per g of product. When the activity of the enzyme of interest is known, the arylsulfatase activity can also be expressed as the as the change in $OD_{410}*10E6/hr$ per unit of activity of enzyme of interest. Activity assay acid lactase: Acid lactase is incubated during 15 minutes with o-nitrophenyl-beta-D-galactopyranoside (Fluka 73660) at pH 4.5 and 37 degrees C. to generate o-nitrophenol. The incubation is stopped by adding 10% sodium carbonate. The extinction of the o-nitrophenol generated is measured at a wave length of 420 nm and quantifies acid lactase activity. One acid lactase unit (ALU) is the amount of enzyme that under the test conditions generates 1 micromol of o-nitrophenol per minute.

Activity Assay Proline-Specific Endoproteases:

Overproduction and chromatographic purification of the proline specific endoprotease from *Aspergillus niger* was accomplished as described in WO 02/45524. The *A. niger* proline specific endoprotease activity was tested using CBZ-Gly-Pro-pNA (Bachem, Bubendorf, Switzerland) as a substrate at 37° C. in a citrate/disodium phosphate buffer pH 4.6. The reaction products were monitored spectrophotometrically at 405 nM. The increase in absorbance at 405 nm in time is a measure for enzyme activity.

The activity of proline-specific endoproteases with near neutral pH optima is established under exactly the same conditions but in this case the enzyme reaction is carried out at pH 7.0.

The activity of proline-specific dipeptidyl peptidases such as DPP IV is established under conditions specified for proline-specific endoproteases with near neutral pH optima, but in this case Gly-Pro-pNA is used as the substrate.

A Proline Protease Unit (PPU) is defined as the quantity of enzyme that releases 1 μmol of p-nitroanilide per minute under the conditions specified and at a substrate concentration of 0.37 mM.

Activity Assay Carboxypeptidases:

The activity of the *A. niger* derived carboxypeptidase PepG ("CPG"; Dal Degan et al., Appl. Env. Microbiol. 58 (1992) 2144-2152) was established using the synthetic substrate FA-Phe-Ala (Bachem, Bubendorf, Switzerland) as a substrate. Enzymatic hydrolysis of this substrate (1.5 mM FA-Phe-Ala at pH 4.5 and 37 degrees C.) results in a decrease of absorbance which is monitored at a wavelength of 340 nm. One unit (CPGU) is the amount of enzyme needed to decrease the optical density at 340 nm by one absorbency unit per minute under the test conditions.

Activity Assay Amino Peptidases.

The activity of aminopeptidases is established using the synthetic substrate X-pNA in which pNA represents p-nitroanilide and "X" an amino acid residue. Because different aminopeptidases can have different selectivities, the nature of amino acid residue "X" depends on the cleavage preference of the aminopeptidase activity tested. Thus, "X" represents the residue for which the specific aminopeptidase has the highest preference. Because many aminopeptidases show the highest reactivity towards Phe, Phe-pNA represents a preferred substrate. Various X-pNA substrates can be obtained from Bachem (Bubendorf, Switzerland). Enzymatic hydrolysis of this substrate (1.5 mM at pH 6.5 and 37 degrees C.) results in a color development which is monitored at a wavelength of 410 nm. One unit (APU) is the amount of enzyme needed to increase the optical density at 410 nm by one absorbency units per minute under the test conditions.

Activity Assay Esterases/Lipases:

Esterases and lipases catalyse the release of free fatty acids from triglycerols. In the present assay glycerol tributyrate is used as the substrate. To establish the esterase/lipase activity, the butyric acid released from tributyrate is titrated with sodium hydroxide to a constant pH of 7.5. Therefore, the amount of sodium hydroxide dosed per time unit in order to keep the pH constant, is directly proportional to the esterase activity of the enzyme sample The measurement is carried out using a Radiometer pH-stat unit and the following reagents.

Arabic Gum solution:Consecutively dissolve, while gently stirring, 100 g Arabic gum (Sigma) and 500 mg Thymol (ICN) in approximately 800 mL demineralised water in a 1 L volumetric flask. Make up to one liter with water and mix. Centrifuge the solution for 15 minutes at 4000 rpm. The resulting arabic gum solution may be kept in the refrigerator for 2 months but should be prepared at least one day before use.

Sodium hydroxide 0.02 mol/l: quantitatively transfer the contents of an ampoule containing 0.01 mol/L NaOH into a 500 mL volumetric flask with water. Make up to volume with water and mix.

SDS/BSA solution: Dissolve, while gently stirring, 1 g SDS (Merck) and 1 g BSA (fraction V, Sigma) in approximately 40 mL water. Prevent the formation of foam. Make up the volume to 1 liter with water after complete dissolving of the SDS and BSA. Only use a freshly prepared solution.

Substrate emulsion: Weigh 50 g glycerol tributyrate in a 600 mL glass beaker and add 300 mL Arabic gum solution. Prepare an emulsion by stirring 5 minutes at maximum speed with the Ultra Turrax. Adjust the pH to 7.5 with NaOH 0.5 mol/L.

To test esterase/lipase activity of a particular enzyme sample, weigh in approximately 1 g of enzyme sample and dissolve in SDS/BSA solution. This sample solution should have a final enzyme content equivalent to approx. 0.2 to 0.8 NBGE/ml (see further). Keep the sample solution on ice until the start of the measurement.

Carry out the measurement by subsequently transferring the following solutions into the heated reaction vessels: 20 mL substrate emulsion, 5.0 mL water (pre-heated at 40° C.) and allow to pre-heat for 15 minutes, then start the measurement by adding 5.0 mL of control sample or the sample solution and start the VIT 90 esterase program of the Radiometer pH-stat unit.

The esterase/lipase unit (NBGE) is defined as the amount of enzyme that releases 1 µmol free fatty acid from glycerol tributyrate per minute at a temperature of 40° C. and pH 7.5 in the following procedure.

EXAMPLES

Example 1

Identification of Off-Flavour Compounds in UHT-Milk

Maxilact LG5000 (DSM, Netherlands) was added under sterile conditions to semi-skimmed UHT milk (Friesche Vlag, Netherlands) to levels of 10,000 and 40,000 NLU per liter and incubated for 4 days at room temperature. In the reference experiment, no Maxilact was added. Prior to assessment of the samples by a taste-panel, a fresh lactase-hydrolyzed milk sample was prepared by adding 40,000 NLU per liter semi-skimmed milk and incubate for 18 hours at room temperature. Sample analysis was performed at NIZO Food Research (The Netherlands) using the SOIR procedure which is a common procedure at NIZO Food Research and which includes a sensory and chemical analysis. Sensory analysis was performed directly on the prepared samples and aliquots of each milk sample were frozen at −25° C. in small portions for further chemical analysis.

Sensory analysis was performed by a 9-membered trained panel. The reference sample was described as cooked, the other samples were classified as not standard UHT milks. The main attributes that described the off-flavour were chemical, medicinal, urine/unclean and stable/manure.

Volatile compounds were isolated with a simultaneous high vacuum distillation near room temperature, creating a watery extract of the sample. The volatile compounds were subsequently isolated from the watery extract using a dynamic headspace and collected at an absorbant. The isolated compounds were injected into a Gas Chromatograph making use of a thermal desorption and separated on a GC-colomn. The GC-effluent was evaluated by two trained assessors (GC-sniff) and described in odour terms (olfactometry). Duplicated high and low concentrated GC-Sniff analyses were carried out by using two different purge times (30 minutes and 24 hours) during dynamic head space sampling. Subsequently the peaks (compounds) indicated during the olfactometric analysis as corresponding with the off-flavour characteristics of the lactase-treated UHT-samples were identified by mass spectrometry. The compounds of interest that may explain the cause of the off-flavour were identified as 1) esters (ethyl butanoate); 2) sulphur compounds (dimethyl sulfide, dimethyl trisulfide and benzothiazole); 3) sulfur esters (methyl thioacetate, methylthiobutyrate); 4) 1-octen-3-ol; 5) 2-nonenal; 6) β-damascenone; 7) borneol and 8) p-cresol. The p-cresol could originate from conjugates in milk. The only compound that was associated with the most offensive sensory attribute 'medicinal' was p-cresol. The concentration of p-cresol in the samples was determined using GC-analysis by addition of standard quantities of p-cresol to the samples. The concentration of p-cresol in the UHT-milk sample 4 days incubation) was estimated at 12 µg per liter. This is clearly above the flavour treshold of 1 ppb and 2 ppb for air and water respectively (Ha et al, (1991) *J Dairy Sci* 74, 3267-3274). It also is in the range of p-cresol-concentrations commonly found in cows milk. The results were confirmed by recombination experiments in milk, confirming that p-cresol is responsible for the medicinal off-flavour in lactase-treated UHT-milk.

Example 2

Determination of Aryl-Sulfatase and β-Galactosidase Activity

Arylsulfatase activity was determined using p-nitrophenylsulfate (obtained from Sigma) as a substrate. For activity measurements, 0.5 ml of substrate solution (20 mM p-nitrophenylsulfate in 100 mM NaP$_i$ buffer pH6.5) was mixed with 0.5 ml sample solution containing the arylsulfatase activity. The solution was incubated at 37° C. for 3 hours. Than the reaction was stopped by addition of 1.5 ml 0.5M NaOH. The OD at 410 nm was determined (1 cm pathlength) against a blank experiment in which water was added instead of sample solution. As reference, a solution was prepared in which the enzyme was added after the reaction was stopped with NaOH. The OD$_{410}$ of this reference solution was subtracted from the OD$_{410}$ determined for the solution in which the enzyme was active for three hours. The sulfatase activity is expressed as the change in OD$_{410}$*10E6/hr and per NLU. The lactase activity (NLU) for the sample solution was determined as given below.

Lactase activity was determined as Neutral Lactase Units (NLU) using o-nitrophenyl-β-D-galactopyranoside (ONPG) as the substrate, according to the procedure described in FCC (fourth ed, July 1996, p 801-802: Lactase (neutral) β-galactosidase activity).

Example 3

Addition of Aryl-Sulfatase to UHT-Milk

The off-flavour test in milk was performed with commercially available arylsulfatase (Sigma, *Aerobacter aerogenes*, type VI; 4.9 mg protein/ml; 3.9 arylsulfatase units as defined by Sigma/mg protein). In the experiment, 50 ml of UHT milk (Campina, The Netherlands) was incubated with 1 ml enzyme solution at 30° C. The development of off-flavour was followed by sniffing the sample. The typical off-flavour smell that was also described in example 1 for the UHT-milk incubated with lactase was clearly noticeable after 2 hours of incubation. The smell was more intense after 17 hours of incubation. Apparently, the aryl-sulfatase generated a similar off-flavour as lactase. Based on the findings, described in example 1, this can be explained by the release of p-cresol from the conjugate p-cresylsulphate in milk. Experiments were also performed in which acid phosphatase (wheat germ, Sigma, 6 phosphatase units as defined by Sigma in 40 ml milk) or glucuronidase (from *E. coli*, Sigma, 6350 glucuronidase units as defined by Sigma per 40 ml milk) were added instead of arylsulfatase. In these incubations the typical off-flavour did not develop. This suggests that the sulphate conjugates are the most important conjugates for the formation of off-flavour in cows milk, This is consistent with literature findings (Lopez et al (1993) *J Agric Food Chem.* 41, 446-454). The results do not completely exclude the presence of other off-flavour compounds, which could be generated by glucuronidase or acid phosphatase but apparently these compounds do not reach levels that are higher than the flavour thresholds.

Example 4

Off-Flavor Test UHT-Milk: Procedure

Semi skimmed UHT milk (Campina, The Netherlands) was incubated with 20,000 NLU/L milk during 48 hours at 30° C. The lactase was added via a sterile filter under sterile conditions to prevent bacterial infection. The milk was tasted after 48 hours by a trained taste panel and compared with a milk solution that was incubated under identical conditions but without addition of lactase. A reference solution was prepared briefly before tasting by adding 5000 NLU/L milk and incubation for 2 hours at 30° C. This sweet milk was used as the reference solution by the taste panel. The off-flavour is scored by the panel as follows: the blank milk was set as '−'. Low off-flavour products containing a noticeable but light off-flavour are given '+', whereas products containing higher amounts of off-flavour are expressed as '++' or '+++'. The indication '+++' indicates a high level of off-flavour, perceived as very unpleasant. Terms used to characterize the off-flavour were the same as those described in example 1.

Example 5

Purification of *K lactis* Lactase: Removal of Aryl-Sulfatase Activity

Maxilact LX5000 (DSM, Netherlands), a commercially available *K. lactis* lactase, was diluted 10 times with water and applied to a Q-Sepharose column (Amersham Biosciences), equilibrated in 55 mM $KP_i$ (pH7.0). Loading was continued until lactase activity was detected in the run-through of the column. The column was subsequently washed with 4 column volumes of 55 mM $KP_i$ (pH7.0), followed by elution of lactase with 65 mM $KP_i$ (pH7.0) containing 0.16M NaCl. Fractions were collected and assayed for lactase activity. The lactase containing fractions were pooled, and loaded on a butyl Sepharose column (Amersham Biosciences) equilibrated in 55 mM $KP_i$ (pH7.) containing 1 M $NaSO_4$. The lactase was applied to the column in presence of 1M $NaSO_4$ (pH7.0) until lactase was detected in the run-through of the column. The column was washed with 4 column volumes of 55 mM $KP_i$ (pH7.) containing 1 M $NaSO_4$ Lactase was eluted using a 15 column volumes inear gradient from 55 mM $KP_i$ (pH7.0) containing 1 M $NaSO_4$ to 55 mM $KP_i$ (pH7.0). The elution profile was monitored by UV-detection (280 nm). Fractions were collected and assayed for lactase activity. Lactase containing fractions were pooled, with omission of those fractions that were collected after the lactase peak (OD 280 nm) had decreased to 50% of the maximum peak value. Omission of these fractions is critical to prevent contamination of the lactase preparation with aryl-sulfatase. The elution of lactase partly overlaps with the elution of arylsulfatase. The product was concentrated and desalted by ultrafiltration on a 10 kdalton filter and preserved by addition of glycerol to 50% w/w.

Example 6

Protease Levels in Purified Lactase

Figure 7:
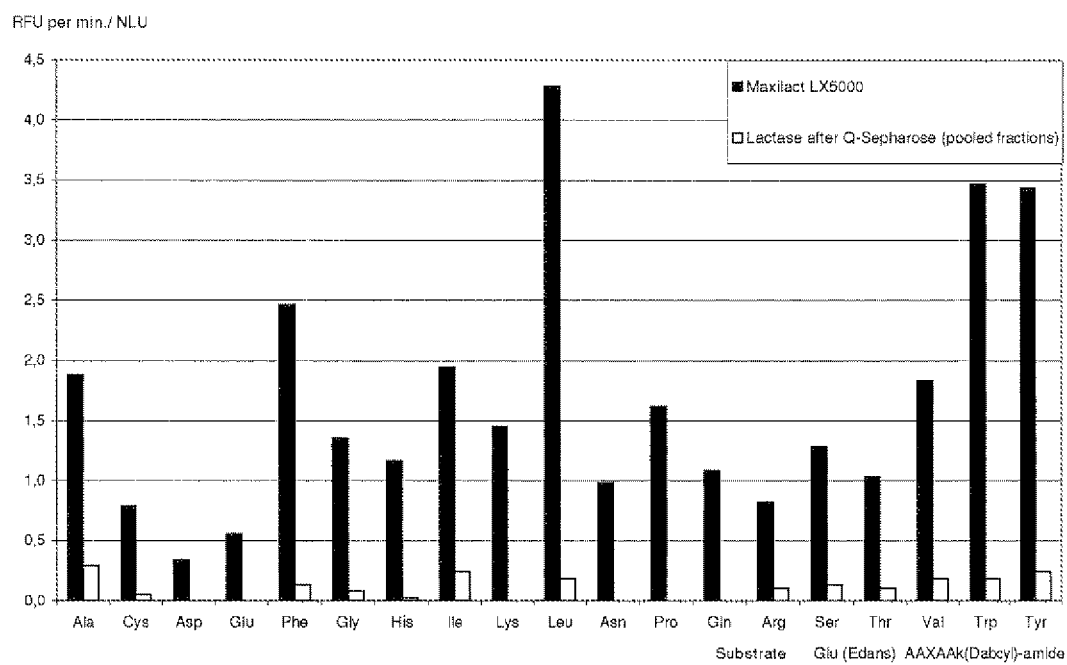
FIG. 7: shows the endoprotease profile using Dabcyl-Edans as substrate.

Protease activity was determined using a series of substrates with the general formula Glu(EDANS)-Ala-Ala-Xxx-Ala-Ala-Lys(DABCYL). (Xxx: any of the 20 natural amino acids). The substrates were obtained from PEPSCAN (Lelystad, The Netherlands), and are internally quenched fluorescent substrates. When such peptide substrates are cleaved, this results in a fluorescent signal. The appearance of fluorescence therefore signals the presence of endo-protease activity. Endo-protease activity was determined in 96-wells microtiter plates by adding 50 µl enzyme solution to 200 µl solution containing 50 µM of the substrate in 100 mM Tris-Bis (pH 6.7). The reaction mixture was incubated for 10 minutes at 40° C. in a TECAN Genius microtiter plate reader using Magellan4 software. Development of fluorescence was followed in time (excitation filter: 340 nm, emission filter: 492 nm). Protease activity was quantified as the slope of the fluorescence line, expressed as RFU/minute/NLU. (RFU: relative fluorescent units, as given by the Genius equipment). NLU-units of the enzyme sample are determined as given in example 2. FIG. 7 shows the enormous reduction in protease activity when LX5000 is purified over the Q-Sepharose column. The pooled fractions after Q-sepharose (example 4) have a factor of at least 5-10 lower protease activity compared to the starting material (LX5000). Lactase samples in which the RFU/min/NLU is <0.5 for each of the substrates used (see FIG. 1) are defined as preparations that have low levels of protease activity.

Example 7

Comparison of Non-Purified and Purified Lactase

Several lactase preparations were submitted to the off-flavour test which is described in example 4. The lactase preparations differed in aryl-sulfatase content. For each preparation, at least two samples were used; individual samples varied in aryl-sulfatase activity, and activity ranges are indicated in the right column of table 1. The results of the off-flavour test are given in table 1. Clearly, levels of arylsulfatase activity are correlated with off-flavour formation. Low levels of aryl-sulfatase (19 or less, see table 1) do not cause off-flavour formation whereas increasing levels lead to increased off-flavour formation. It is also clear that the lactase preparation after Q-Sepharose still shows off-flavour development, even though the protease levels are low (see example 5).

TABLE 1

Off flavour development for various lactase preparations.

| Lactase preparation | Level of off-flavour formation | Aryl sulfatase activity in preparation delta OD * 10E6/hr per NLU |
|---|---|---|
| Milk without addition | − | 0 |
| Lactase after Q-Sepharose (pooled fractions; example 4) | + to ++ | 100-300 |

TABLE 1-continued

Off flavour development for various lactase preparations.

| Lactase preparation | Level of off-flavour formation | Aryl sulfatase activity in preparation delta OD * 10E6/hr per NLU |
|---|---|---|
| Lactase GODO YNL-2 (GODO, Japan) | + | 40-120 |
| Lactase after butyl sepharose (pooled fractions; example 4) | − | <8-19[2] |
| Lactase containing high aryl-sulfatase[1] | +++ | 723 |

[1]Fraction with high aryl-sulfatase activity, selected from the Q-Sepharose elution fractions described in example 4.
[2]the level of 8 arylsulfatase units (as defined in example 2) is the detection limit of the assay. <8 means no arylsulfatase activity was observed.

Example 8

Different Commercial Enzyme Preparations Contain Arylsulfatase Activity

Various enzyme products produced from different sources and recovered by different processing routes were collected and were analysed for arylsulfatase activity using the assay specified in the Materials & Methods section. From the results obtained (see Table 2), it is clear that enzyme preparations obtained from various microorganisms such as *Aspergillus oryzae, Kluyveromyces lactis, Rhizomucor miehei, Talaromyces emersonii* and *Trichoderma harzianum* can be seriously contaminated with arylsulfatase activity.

These enzyme preparations can advantageously be purified by the process according to the invention.

TABLE 2

Aryl sulfatase activity in various commercial enzyme preparations

| Enzyme product | Supplier | batch code | Prod. organism | arylsulfatase activity (in delta OD * 10E6/hr per g or ml of enzyme preparation) |
|---|---|---|---|---|
| Sumizyme FP (microbial proteases) | Shin-Nihon | U-ES29 (chem syst.) | A. oryzae | 39300*10E3 U/g |
| Sumizyme LP (microbial proteases) | Shin-Nihon | S-9906-02 | A. oryzae | 14950*10E3 U/g |
| Maxilact LG2000 | DSM | AE0050 | K. lactis | 283*10E3 U/ml |
| Acid lactase | Amano | LAFD10505 08 (20 mg)* 3.3 h reaction | A. oryzae | 12550*10E3 U/g |
| Lipase F-AP15 (lipases) | Amano | LFB 1251507 | A. oryzae | 1230*10E3 U/g |
| Piccantase A (microbial esterase/lipase) | DSM | F5583 (20 mg) | R. miehei | 250*10E3 U/g |
| Filtrase BR-X β-glucanase (microbial hemicellulases) | DSM | AF0392 | T. emmersonii | 513*10E3 U/ml |
| Oenozyme Elevage β-glucanase (microbial hemicellulases) | DSM | KM616001 | T. harzianum | 1985*10E3 U/g |

Example 9

Chromatographic Removal of Arylsulfatase Activity from the Proline-Specific Protease from *Aspergillus niger* Using Ion Exchange Chromatography In order to remove the arylsulfatase side activities from the proline-specific endoprotease secreted by *A. niger* (WO 02/046381), a number of chromatographic resins were screened. Because the isoelectric points of the protease and the main secreted arylsulfatase activities secreted by *A. niger* were found to be approximately 0.5 pH units apart, the identification of a chromatographic separation that allows an acceptable separation of the two activities, even under large scale, industrial conditions, is quite demanding.

Finally, the cation exchanger SP Sepharose 6FF and the hydrophobic interaction (HIC) resin butyl Sepharose 6FF (Amersham Biosciences Europe) were selected. for further tests. Both resins were tested in Tricorn 5/100 columns (CV=2.2 ml) using an ÄKTA Explorer 100 controlled by UNICORN 3.20 and an ÄKTA Purifier controlled by UNICORN 3.21 in combination with a FRAC-950 fraction collector. After elution all fractions generated were tested for proline-specific endoprotease activity and arylsulfatase activity using methods specified in the Materials and Methods section.

TABLE 3

Conditions under which the SP-Sepharose-6FF chromatography was conducted:

| | |
|---|---|
| Buffer A | 20 mM Citrat, 0.085M NaCl, pH 3.0 |
| Buffer B | 20 mM Citrat, 1.0M NaCl, pH 3.0 |
| Start conc. B (%)/Start cond. (mS/cm) | 0/10.7 |
| Flow rate (ml/min) | 0.48 |
| Sample volume (ml) | 0.40 |
| Wash volume (CV) | 6.1 |
| Flow through and wash fraction sizes (ml) | 1.0 and 11.0 |
| Gradient | 0-40% B in 10 CV; 100% for 3 CV |
| Eluate fraction size (ml) | 1.0 |

After pooling of the fractions showing proline-specific activity towards the chromogenic peptide Z-Gly-Pro-pNA (Bachem, Bubendorf, Switzerland), arylsulfatase activities of the crude and chromatographically purified enzyme preparations were compared. It turned out that in preparations showing exactly the same proline-specific activity (9 PPU/ml), the arylsulfatase activity was lowered from 3800*10E3 units/ml in the crude preparation to less than 30*10E3 units/ml in the chromatographically purified preparation.

Example 10

Chromatographic Removal of Arylsulfatase Activity from the Proline-Specific Protease from *Aspergillus niger* Using Hydrophobic Interaction Chromatography The HIC chromatography was conducted under the following conditions. A diafiltrate of the *A. niger* derived proline-specific endoprotease having an activity of 10 PPU/ml was used as the starting material. This diafiltrate was diluted two times with 20 mM citrate buffer containing 2 M $Na_2SO_4$ (pH 4.2, G=121 mS/cm) and was subsequently sterilized by filtration (0.2 µm) before loading on the column.

TABLE 4

Conditions under which purification of example 10 is performed.

| | |
|---|---|
| Resin | Butyl Sepharose 6 FF |
| Column type | XK26 |
| Column volume (ml) | 107 |
| Buffer A | 20 mM citrate + 1M $Na_2SO_4$ (pH 4.2; G = 94 mS/cm) |
| Buffer B | 20 mM citrate + 0.02M $Na_2SO_4$ (pH 4.2; G = 6 mS/cm) |
| Flow rate (ml/min) | 15 (or 170 cm/h) |
| Equilibration | 0 or 20% buffer B (94 or 82 mS/cm) |
| Sample volume (ml) | 76-77 ml (with 1 M $Na_2SO_4$ as end concentration) |
| Wash | 20% buffer B (83 mS/cm) for 24 CV |
| Flow through and wash fraction sizes (ml) | 38.5 ml and collection of total wash volume or total selection of flow through and wash |
| Elution (step) | 100% buffer B for 12 or 15 CV |
| Eluate fraction size (ml) | 10 or 50 ml |

As the result of a considerable tailing after loading of the enzyme on the column, a long washing procedure was required to obtain baseline separation. Finally, the proline-specific endoprotease could be eluted from the column with buffer B. The fractions containing the proline-specific proteolytic activity were pooled. Though diluted, this purified material showed significantly lowered arylsulfatase activity if calculated back to the original proteolytic activity demonstrating that the proline-specific endoproteolytic activity and the arylsulfatase activity were effectively separated using this hydrophobic interaction chromatography protocol. Also here it turned out that in preparations showing exactly the same proline-specific activity (9 PPU/ml), the arylsulfatase activity was lowered from 3800*10E3 units/ml in the crude preparation to less than 30*10E3 units/ml in the chromatographically purified preparation.

Example 11

The Purified Proline-Specific Endoprotease from *A. niger* Generates Casein Hydrolysates without Off Odors To test the performance of the chromatographically purified proline-specific endoprotease, two casein hydrolysates were prepared using a chromatographically purified and a non-chromatographically purified proline-specific endoprotease in exactly the same protocols.

To a solution containing 100 g/L of sodium caseinate (Murray Goldbern, New Zealand) and water, subtilisin (Protex^ L; 25 milliliter/gram protein was added and incubated for 4 hours at 60° C. and a pH as is. The precipitate formed slowly dissolved while stirring. At the end, a clarified solution was obtained with a minor precipitate. Then pH of the solution was adjusted to pH 4.5 and the liquid was split into equal volumes. To one of these volumes, 1 PPU of a crude *A. niger* prolyl endopeptidase per gram of casein hydrolysate was added; to the other volume 1 PPU of a chromatographically purified *A. niger* prolyl endopeptidase. Incubation was continued for 9 hours at 55° C. followed by a 10 kDa ultrafiltration for both solutions. After a further heat inactivation step (5 second 120 degrees C.) and a cooling down period, the taste and the odor of the two liquids were evaluated by a panel of 5 people trained in detecting and ranking off flavours and off odors in milk hydrolysates. The panel was unanimous in their conclusion that the hydrolysate prepared with the crude proline-specific endoprotease had a characteristic, "barn-like" odour and flavor which was missing in the preparation prepared with the chromatographically purified proline-specific endoprotease.

TABLE 5 overview of results of examples 11 and 13

| | In enzyme preparation | | In substrate (during application) | |
|---|---|---|---|---|
| | AS-activity (In Delta $OD*10^6$/hr per ml) | AS-activity (In Delta $OD*10^6$/hr per PPU) | AS-activity in substrate (in Delta $OD*10^6$ per liter of substrate) | |
| Crude preparation "proline- | $3.8*10^6$ | $422*10^3$ | $42*10^6$ | Barn-like flavour |

TABLE 5-continued overview of results of examples 11 and 13

|  | In enzyme preparation | | In substrate (during application) |  |
|---|---|---|---|---|
|  | AS-activity (In Delta $OD*10^6$/hr per ml) | AS-activity (In Delta $OD*10^6$/hr per PPU) | AS-activity in substrate (in Delta $OD*10^6$ per liter of substrate) |  |
| specific" (9 PPU/ml) Purified preparation "proline-specific" (9 PPU/ml) | $30*10^3$ | $3.3*10^3$ | $330*10^3$ | No barn-like flavour |
| Crude preparation "carboxy-peptidase" (2060 CPG/ml) | $31.2*10^6$ | $15.1*10^3$ | $3.2*10^6$ | off-flavour |
| Crude preparation "carboxy-peptidase" (2060 CPG/ml) | $10*10^3$ | 4.8 | 960 | No off-flavour |

Example 12

Chromatographic Removal of Arylsulfatase Activity from a Carboxypeptidase from *Aspergillus niger*

Because the isoelectric points of the carboxypeptidase (i.e. p. 4.5) and the main secreted arylsulfatases from *A. niger* (i.e. p.'s of 5.0 and 5.4) are close together, chromatographic separation of the two enzymes proved to be quite difficult. However, the following procedure allowed us to obtain a pure carboxypeptidase, free from arylsulfatase activity. Most importantly, the method is relatively simple so that it can be carried out on an industrial scale.

Again a SP-Sepharose FF resin was used. The chromatography was conducted under the following conditions:

TABLE 6 conditions under which chromatography of example 12 is performed
Buffer A: 20 mM NaCitrate + 40 mM NaCl pH 3.1 ± 0.1;
conductivity 5.5 ± 0.3 mS/cm
Buffer B: 20 mM NaCitrate pH 5 ± 0.2; conductivity 3 mS/cm

| Equilibration: | PH 3.1 ± 0.1; cond 5.5 ± 0.3 mS/cm | 5 | cv |
| Load | 3100 U/ml resin | 7 | cv |
| Washing | Buffer A | 10 | cv |
| Elution buffer | Buffer B | 4 | cv |
| Collected pepG | Buffer B | 1.3-1.5 | cv |
| Caustic cleaning | 1 M NaOH | 2 | cv |

After the crude enzyme was applied to the column, the column was washed with buffer A to remove unbound/slightly bound contaminations. Finally, the carboxypeptidase is eluted with buffer B. The peak containing activity towards the hydrolysis of the chromogenic peptide FA-Phe-Ala-OH (Bachem, Bubendorf, Switserland) was collected. In carboxypeptidase preparations containing comparable carboxypeptidase activities (2060 CPG/g; see Materials and Methods for the activity determination), the arylsulfatase activity decreases from an initial 31200*10E3 units/ml in the crude enzyme to 10*10E3 units/ml in the purified preparation.

Example 13

The Purified Carboxypeptidase from *A. niger* Accelerates the Aging of Gouda Cheeses without Generating Off-Flavours Milk was unstandardised and collected from the NIZO. Gouda cheese was manufactured using the NIZO method. Briefly: After starter addition, stir for 15-20 minutes. Then add rennet, stir for 3 minutes and set (approx. 45-50 minutes). Cut coagulum using the gradual increase dial. This will take 10 minutes and have a final speed of 8.5. Turn the blades and stir for another 10 minutes at speed 11. Drain till 120 L remains in vat. Add 36 L (30% of remaining volume) of water at 55° C. to achieve an end temperature in the vat of 35.5-35.7° C. while stirring at speed 16. Stir for 60 minutes at speed 16. Collect the curd and rest for 15 minutes. Divide the curd over the moulds (weight) and rest the filled moulds for 30 minutes. Press for 30 minutes at 0.7 bar (add the cheese code after first pressing), 30 minutes at 1.2 bar and then another 30 minutes at 1.7 bar. Turn the curd after each. After pressing, the pressure is removed and the cheeses are rested in the moulds (overnight in the brining room at 13° C.). The cheeses are removed from the moulds and entered into the brine for 30 hours and turned twice to ensure uniform brining. Ripening at 13° C., 88% humidity. The method standardizes at 1.05 fat to protein ratio (equivalent to about 0.85 fat to casein Following pasteurisation, the milk was pumped into the 200 L cheese vats. Delvo®-TEC UX21A (1.5 U; DSM Food Specialities, Delft, The Netherlands) was used as starter culture and Maxiren® 600 (55 IMCU/L milk; DSM Food Specialities, Delft, The Netherlands) as rennet. The cheeses were brined for 26 hours and ripened at 13° C., 88% RH. Purified and non-purified PepG was added with the rennet at a level of 200 CPGU/liter milk.

Following 6 and 24 weeks of ripening, representative samples of a cheese from each cheese vat were graded using an internal panel. These sessions have taken place in a round-the-place manner which means that the graders are informed of the trial details and afterwards discuss their findings which are then summarised.

TABLE 7

| results of example 13: 6 weeks (n = 7) | |
|---|---|
| Control | Young Gouda cheese, no off flavours, little bit acid and buttery odour. |
| Purified PepG | More mature Gouda cheese, farmhouse type flavours, a strong odour and a fuller flavour. |
| Unpurified PepG | Like the purified PepG cheese only bitter notes in the flavour and after taste. |

TABLE 8

| results of example 13: 24 weeks (n = 6) | |
|---|---|
| Control | Mature Gouda cheese, bit salty |
| Purified PepG | Cheese with an intense flavour, touch of sweetness |
| Unpurified PepG | Very piquant flavoured cheese, farmhouse cheese, not in balance, off flavour |

A clear effect was found as a result of the addition of PepG, both purified and unpurified. The bitter notes and the disbalances recorded for the cheeses in which the non-purified was used lead to the conclusion that PepG should be purified.

Examples 14-15

In the examples described hereinbelow, standard molecular cloning techniques such as isolation and purification of nucleic acids, electrophoresis of nucleic acids, enzymatic modification, cleavage and/or amplification of nucleic acids, transformation of E. coli, etc., were performed as described in the literature (Sambrook et al. (2000) "Molecular Cloning: a laboratory manual", third edition, Cold Spring Harbor Laboratories, Cold Spring Harbor, N.Y., and Innis et al. (eds.) (1990) "PCR protocols, a guide to methods and applications" Academic Press, San Diego).

Example 14

Construction of an Arylsulfatase Knock-Out Strain of Kluyveromyces lactis

Isolation of Kluyveromyces lactis Chromosomal DNA:
A 100 ml YEPD (1% Yeast-extract; 1% Bacto-peptone; 2% glucose) shake flask was inoculated with a single colony of K. lactis CBS 2359 and cultivated for 24 hours at 30° C. shaking at 280 rpm. The amount of cells was counted using a counting chamber and an amount of culture corresponding to $4.1*10^8$ cells was used. Extraction of chromosomal DNA was performed using the Fast DNA Spin Kit supplied by Q-BIOgene (Cat#6540-600). The yeast protocol was used: one homogenizing step using the Fastprep FP120 homogenizer (BIO101 Savant) of 40 seconds at speed setting 6.0 was used. Subsequently the sample was cooled on ice and subsequently homogenized again using the same conditions.
The purity and yield of the extracted genomic DNA was determined using the Nanodrop ND1000 spectrofotometer. It was found that the concentration of the extract was 114 nanogram/microliter. The A260/280 and A260/230 ratio was found to be respectively 1.57 and 0.77.
PCR Amplification of 5' and 3' Arylsulfatase Flanks:

```
5' flank arylsulphatase primers:
DFS-15289 (5'→3'):
TCG CCG CGG TTG TCA ACT ATA TTA ACT ATG

DFS-15290 (5'→3'):
GAT AGA TCA TAG AGT AAC AAT TGG

3' flank arylsulphatase:
DFS-15291 (5'→3'):
GCA ACT GAA GGT GGT ATC AAT TG

DFS-15292 (5'→3'):
CAC CCG CGG CAC CAG ATA ATG GAG GTA G

3' flank SacII arylsulphatase:
DFS-15291 (5'→3'):
GCA ACT GAA GGT GGT ATC AAT TG

DFS-15340 (5'→3'):
CGG CAC CAG ATA ATG GAG GT
```

The arylsulfatase flanks were amplified using Phusion High-Fidelity DNA Polymerase, (Finnzymes, Espoo Finland). The K. lactis CBS 2359 genomic DNA was diluted 100 times with Milli-Q water and 5 µl was used as a template in a 50 µl PCR mix, according to suppliers' instructions. A Hybaid MBS 0.2G PCR block using the following programs:

| PCR Program 5' flank arylsulfatase: | |
|---|---|
| Stage 1 (1 cycle) | 98° C. 30 s |
| Stage 2 (30 cycles) | 98° C. 10 s |
| | 60° C. 30 s |
| | 72° C. 30 s |
| Stage 3 (1 cycle) | 72° C. 10 min |
| | 4° C. Hold |
| PCR Program 3' flank arylsulphatase: | |
| Stage 1 (1 cycle) | 98° C. 30 s |
| Stage 2 (30 cycles) | 98° C. 10 s |
| | 72° C. 30 s |
| | 72° C. 30 s |
| Stage 3 (1 cycle) | 72° C. 10 min |
| | 4° C. Hold |
| PCR Program 3' flank SacII⁻ arylsulphatase: | |
| Stage 1 (1 cycle) | 98° C. 30 s |
| Stage 2 (30 cycles) | 98° C. 10 s |
| | 65° C. 30 s |
| | 72° C. 30 s |
| Stage 3 (1 cycle) | 72° C. 10 min |
| | 4° C. Hold |

Construction of an Arylsulphatase Knock-Out Vector
The obtained 5'-, 3'- and 3' SacII⁻ arylsulfatase flank PCR fragments were cloned into the pCR-Blunt II-TOPO vector using the Zero Blunt TOPO PCR Cloning Kit (Invitrogen; Part. no. 45-0245), according to suppliers' instructions. The TOPO cloning reactions were transformed to One Shot TOP10 Chemically Competent E. coli (Invitrogen; Part. no. 44-0301) according to suppliers' instructions. Correct clones were selected based on restriction pattern analysis using MunI, SacII, XcmI, and DraI; MunI, SacII, EcoRI and EcoRV; MunI, EcoRI, EcoRV and SacII for respectievely, 5' TOPO, 3' TOPO and 3' SacII⁻ TOPO.
The amds cassette was isolated from the pKLAC1 vector (New England Biolabs). The pKLAC1 plasmid was transformed to chemically competent dam-Idcm-E. coli cells (New England Biolabs; Cat. No C2925H) and the un-methylated plasmid was isolated.
Large plasmid DNA batches of 5' TOPO, 3' TOPO, 3' SacII⁻ TOPO and pKLAC1 vector were isolated from overnight LBC cultures containing 50 µg/ml Kanamycin using the GeneElute Plasmid MidiPrep Kit (Sigma; Cat. No. NA0200).
The pKLAC1 vector was digested SalI and XbaI and the 5' TOPO vector was digested XbaI and XhoI. Digests were purified using the Nucleospin ExtractII Kit (Machery Nagel) according to suppliers' instructions.

The SalI/XbaI digested amdS cassette was ligated into the XbaI/XhoI digested 5' TOPO vector using the Quick ligation Kit (New England Biolabs; Cat. No. M2200S) according to suppliers' instructions. The ligation mix was transformed to One Shot TOP10 Chemically Competent *E. coli* (Invitrogen; Part. no. 44-0301) according to suppliers' instructions. A correct clone was selected based on restriction pattern analysis using MunI, EcoRI and SacI. This resulted in the following vector: 5' amdS TOPO vector (FIG. 1)

A large batch of the 5'amdS TOPO plasmid was isolated from overnight LBC cultures containing 50 μg/ml Kanamycin using the GeneElute Plasmid MidiPrep Kit (Sigma; Cat. No. NA0200) according to suppliers' instructions. The 5'amdS TOPO vector was digested MunI and AscI and the 3' SacII⁻ TOPO vector was digested MunI and EcoRI. The MunI/EcoRI 3' SacII⁻ TOPO fragment was isolated and purified by means of gel extraction. An electrophoresis was performed on 1% agarose in TAE buffer containing SYBR Safe DNA Stain (Invitrogen; Cat. No. S33102), according to suppliers' instructions. The fragment was visualized using the dark reader transilluminator (Clare Chemical Research; Cat. No. DR-45M), excised from the gel and extracted from the agarose using the Nucleospin ExtractII kit (Machery Nagel; Cat. No. 740 609.250) according to suppliers' gel extraction protocol.

The 5'amdS TOPO vector was digested MunI and AscI and purified using the Nucleospin ExtractII Kit (Machery Nagel) according to suppliers' PCR purification protocol. Subsequently the MunI/AscI digested 5'amdS TOPO vector was dephosphorylated using Shrimp Alkaline Phosphatase (Roche; Cat. No. 1 758 250) according to suppliers' instructions.

The MunI/EcoRI 3' SacII⁻ TOPO fragment was ligated into the dephosphorylated MunI/AscI digested 5' amdS TOPO vector using the Quick ligation Kit (New England Biolabs; Cat. No. M2200S) according to suppliers' instructions. The ligation mix was transformed to chemically competent dam-/dcm-*E. coli* cells, (New England Biolabs; Cat. No C2925H) according to suppliers' instructions. A correct clone was selected based on restriction pattern analysis using EcoRI and EcoRV. This resulted in the following vector: 5' amdS 3' SacII– TOPO vector.

A large batch of 5' amdS 3' SacII⁻ TOPO vector was isolated from overnight LBC cultures containing 50 μg/ml Kanamycin using the GeneElute Plasmid MidiPrep Kit (Sigma; Cat. No. NA0200) according to suppliers' instructions.

Figure 3:
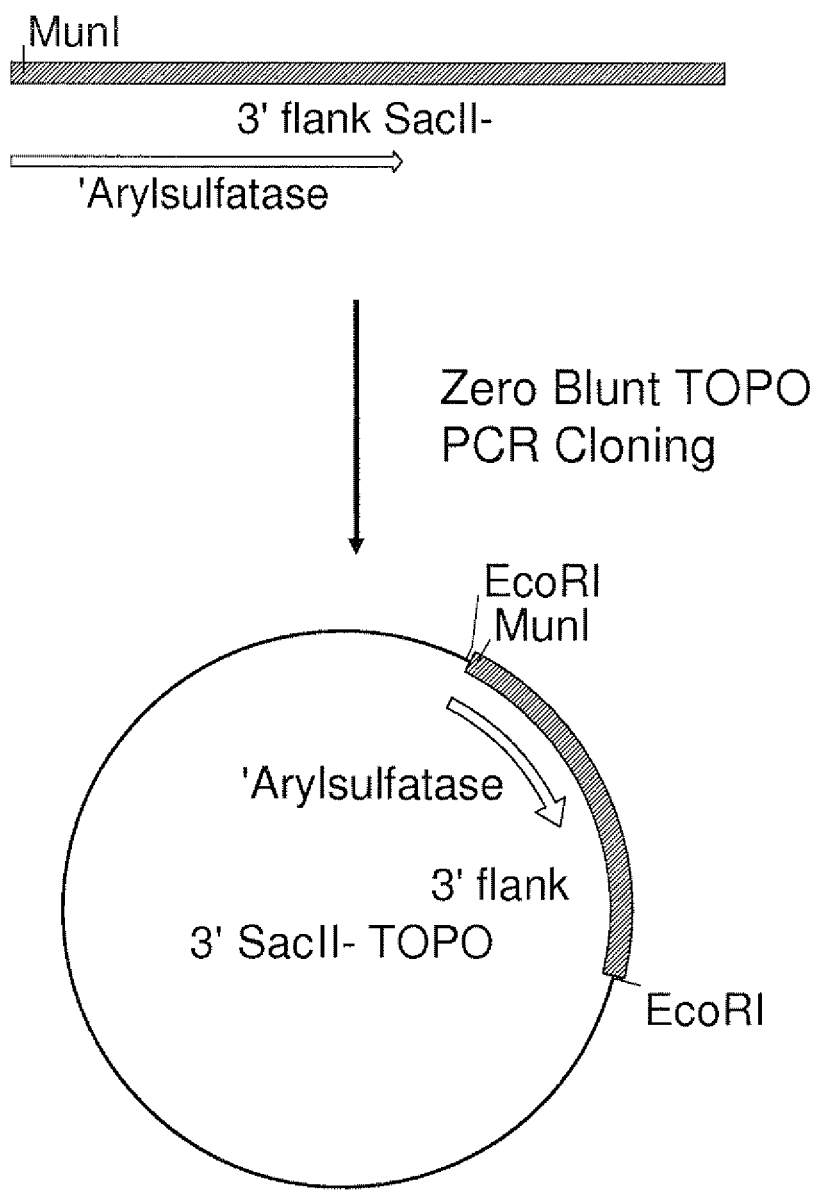
FIG. 3: Cloning of the 3'-flank of the *K. lactis* arylsulfatase gene, lacking the SacII site, in TOPO vector
Figure 4:
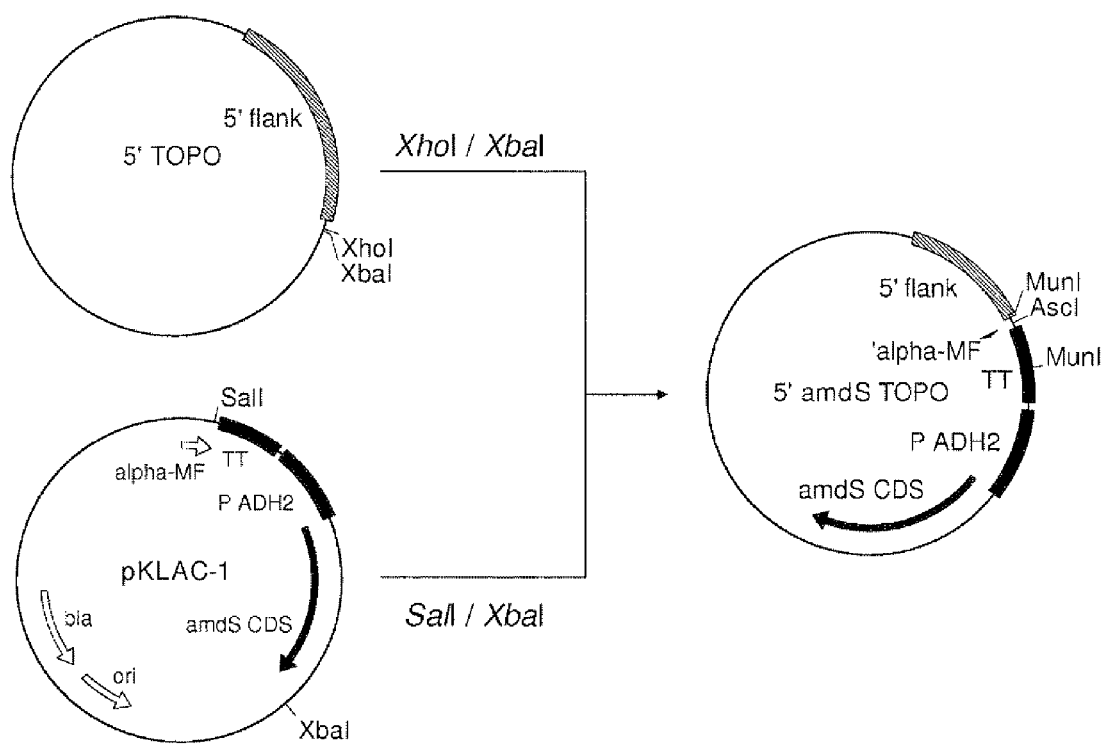
FIG. 4: Combining the 5'-flank and the amdS selection cassette in one plasmid
Figure 5:
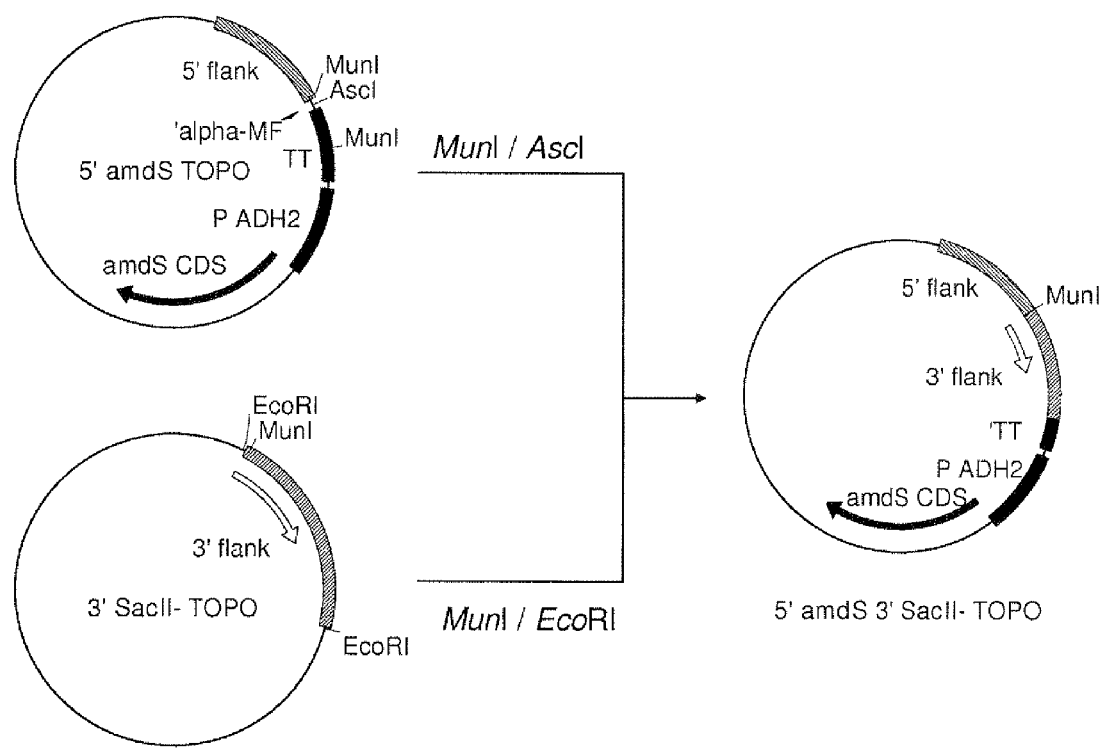
FIG. 5: Combining the 5'-flank, 3'-flank and the amdS selection cassette in one plasmid
Figure 6:
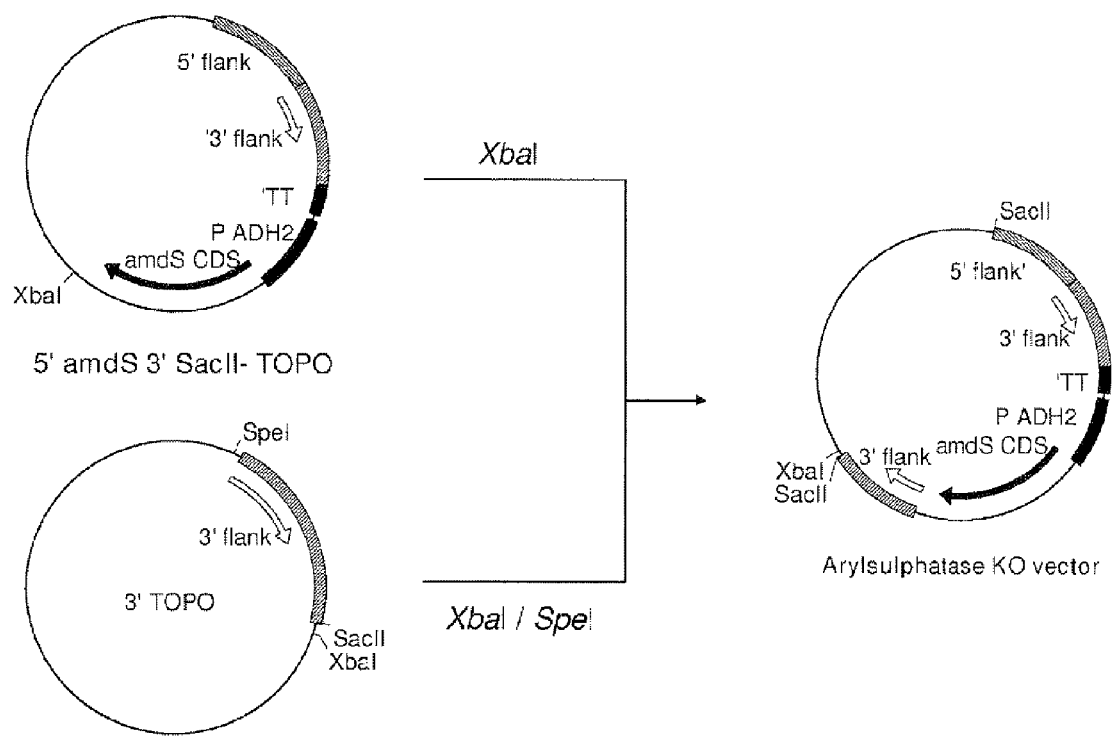
FIG. 6: Final construction of the arylsulfatase knockout construct

The 5'amdS 3'SacII⁻ vector was digested with XbaI. The 3' TOPO vector was digested with XbaI and SpeI. Digests were purified using the Nucleospin ExtractII Kit (Machery Nagel) according to suppliers' instructions. The XbaI/SpeI 3' TOPO fragment was isolated by means of gel extraction, as described above. The XbaI digested 5'amdS 3'SacII⁻ vector was dephosphorylated using Shrimp Alkaline Phosphatase, Roche (Cat. No. 1 758 250) according to suppliers' instructions. The XbaI/SpeI 3' fragment was ligated in the dephoshorylated XbaI digested 5' amdS 3' SacII⁻ vector using the Quick ligation Kit (New England Biolabs; Cat. No. M2200S) according to suppliers' instructions. The ligation mix was transformed to One Shot TOP10 Chemically Competent *E. coli* (Invitrogen; Part. no. 44-0301). A correct clone was selected based on restriction pattern analysis using MfeI, KpnI, EcoRI, SacII, ScaI. This resulted in the final *K. lactis* arylsulphatase knock-out vector (FIG. 3).

A large batch of the arylsulphatase knock-out vector was isolated from overnight LBC cultures containing 50 μg/ml Kanamycin using the GeneElute Plasmid MidiPrep Kit (Sigma; Cat. No. NA0200) according to suppliers' instructions. The *K. lactis* arylsulphatase knock-out vector was digested with SacII so the linear knock-out cassette would be obtained, lacking the TOPO vector part. The digest was purified using the Nucleospin ExtractII Kit (Machery Nagel) according to suppliers' instructions.

Transformation of *K. lactis* CBS 2359 with arylsulphatase knock-out vector A 100 ml YEPD culture of *K. lactis* CBS2359 was incubated at 30° C., shaking at 280 rpm for 24 hours. This culture was used to inoculate a 100 ml YEPD culture which was grown under the same conditions until an OD610 between 0.5 and 0.8 was reached.

Cells were harvested by means of centrifugation for 5 minutes at 1559 g and 4° C. The cell pellet is washed with 50 ml sterile electroporation buffer (EB): 10 mM Tris pH 7.5, 9.2% (w/v) Sucrose, 1 mM MgCl$_2$ at 4° C. The cell pellet was resuspended in 50 ml YEPD containing 25 mM DTT and 20 mM HEPES buffer pH 8.0 at room temperature. The cells were incubated 30 minutes at 30° C. without shaking. The cells were harvested by means of centrifugation for 5 minutes at 1559 g and 4° C. and washed with 10 ml ice cold EB. The cells were again pelletted by means of centrifugation for 5 minutes at 1559 g and 4° C. and resuspended in 0.1 ml ice cold EB. The cell suspension was distributed in microliter aliquots in 1.5 ml eppendorf tubes. To one aliquot of cells 0.2-1.0 microgram (1-5 microliter) of the linear knock out construct was added, mixed by pipetting and incubated on ice for 15 minutes. The cell-DNA mix was added to a chilled electroporation cuvette with a 2 mm gap size (BTX; Part. No. 45-0125). Electroporation was performed on a BioRad electroporator composed of a Gene Pulser (BioRad, Model No. 1652077) and a Pulse Controler (BioRad, Model No. 1652098) using the following settings: 1000 V, 400 Ohm and 25 μF. Immediately after electroporation 1 ml YEPD was added and the cells were transferred to a sterile 12 ml tube and incubated during 2 hours in an shaking incubator at 30° C. The cells were pelletted for 5 minutes at 1559 g and washed in fysiologic saline solution (0.85% (w/v) sodium chloride). The cells were again pelletted and resuspended in 1 ml fysiologic saline solution. Several aliquots of 25 μl, 50 μl and 100 μl were plated on selective amdS agar plates: 1.25% (w/v) agar, 1.17% (w/v) Yeast Carbon Base, 30 mM phosphate buffer pH 6.8 and 5 mM acetamide. Plates were incubated for 2 days at 30° C. followed by 2 days incubation at room temperature.

Colonies were selected and purified by streaking them on YEPD agar plates so single colonies would appear and incubated at 30° C. for 24 hours. These single colonies were tested for targeted integration of the knockout construct using a colony PCR with oligonucleotides targeted against the amdS cassette and downstream of the integrated knock out construct. Colony material was suspended in 20 mM NaOH, 0.2% (w/v) and incubated for 5' at 98° C. The cell suspension was diluted 2 times with water and 2.5 microliter was used directly as template in a 25 microliter PCR reaction using Phusion High-Fidelity DNA Polymerase (Finnzymes; Espoo Finland; Product code F-530S) according to suppliers' instructions.

```
Fw 3' amdS:      GAC AAT TGA TAC CAC CTT CAG TTG

Rv downstream:   CTG GGA AAT GTG GTG ACT CCA TA
```

Program Targeting PCR:

| | |
|---|---|
| Stage 1 (1 cycle) | 98° C. 30 s |
| Stage 2 (30 cycles) | 98° C. 10 s |
| | 68° C. 30 s |
| | 72° C. 30 s |
| Stage 3 (1 cycle) | 72° C. 10 min |
| | 4° C. Hold |

PCR was analysed on 1% agarose gels and targeted transformants that show a clear amplified band were selected. The arylsulfatase knockout strains were named 2359ΔARY1-10, and stored until further use.

Example 15

Detection of Arylsulfatase Activity in 2359ΔARY

Motherstrain CBS 2359 and strain 2359ΔARY were all cultivated in shakeflask in 100 ml YEP+2% galactose for 3 days at 30° C. Biomass was collected by centrifugation for 5 minutes at 1559 g and 4° C. Biomass was washed twice with ice-cold water to remove medium components. Yeast biomass was treated with Yeast Protein Extraction reagent (Y-PER) according the instructions of the manufacturer (Pierce), to extract intracellular enzymes like arylsulfatase. It will be clear to those skilled in the art that other yeast lysis protocols can be used to extract arylsulfatase activity, like mechanical sheering with glasbeads, or enzymatic treatment to dissolve the cell wall with e.g. Zymolyase (see i.e. Glover and Hames, DNA cloning 2—a practical approach, IRL Press 1995).

Arylsulfatase was measured in the extract using the method described in Example 2. From this experiment it became clear that while the motherstrain contained an appreciable amount of arylsulfatase activity, no such activity could be detected in the 2359ΔARY strain. When the β-galactosidase (lactase) activity was measured in this extract according to Example 2, no difference in lactase activity could be detected between the wild type strain CBS 2359 and the mutant strain 2359ΔARY, showing that the mutant strain is specifically disturbed in arylsulfatase activity.

The mutant strain can be used to make a lactase preparation at industrial scale, virtually devoid of arylsulfatase activity.

The invention claimed is:

1. A process for producing a dairy product which comprises adding a lactase obtained from yeast to a dairy product comprising lactose, wherein said lactase comprises less than 40 units arylsulfatase activity per NLU of lactase activity.

2. The process of claim 1 wherein the dairy product produced is free of off-flavours produced by arylsulfatase.

3. The process according to claim 2, wherein said dairy product contains an alkyl phenol substituted with a sulfate group.

4. The process according to claim 2, wherein the dairy product contains milk protein.

5. The process according to claim 2, wherein the dairy product is selected from the group consisting of milk and a fermented milk product.

6. The process according to claim 2, wherein the level of arylsulfatase in the dairy product during said treating is at most 500*10E3 arylsulfatase units per liter of dairy product.

7. A dairy product obtainable by the process according to claim 2.

8. The process according to claim 4, wherein the milk protein is selected from the group consisting of casein and whey protein.

9. The process according to claim 5, wherein the fermented milk product is yoghurt, whey or a hydrolysate.

10. The process according to claim 6, wherein the level of arylsulfatase in the dairy product during said treating is at most 250*10E3 arylsulfatase units per liter of dairy product.

11. The process according to claim 10, wherein the level of arylsulfatase in the dairy product during said treating is at most 100*10E3 arylsulfatase units per liter of dairy product.

12. The process according to claim 10, wherein the level of arylsulfatase in the dairy product during said treating is at most 50*10E3 arylsulfatase units per liter of dairy product.

13. The process according to claim 10, wherein the level of arylsulfatase in the dairy product during said treating is at most 25*10E3 arylsulfatase units per liter of dairy product.

14. The process of claim 2, wherein said lactase is obtained by:
(a) separation of arylsulfatase using chromatography from a preparation which comprises lactase and arylsulfatase,
(b) cultivating a lactase expressing cell in growth medium to which sulphate has been added to repress arylsulfatase expression,
(c) using a lactase expressing cell in which the gene for arylsulfatase is eliminated or disrupted; or
(d) using a lactase expressing strain having less than 10% of the detectable intracellular or extracellular arylsulfatase activity of the wild type strain from which the lactase expressing strain originates.

15. The process according to claim 14, wherein said lactase is neutral lactase.

16. The process according to claim 14, wherein said lactase is neutral lactase from *Kluyveromyces lactis*.

17. The process according to claim 14, wherein said lactase is a neutral lactase derived from the cytoplasm of yeast.

18. The process according to claim 14, wherein said off flavor is medicinal.

19. The process according to claim 14, wherein said lactase expressing strain has less than 5% of the detectable intracellular or extracellular arylsulfatase activity of the wild type strain from which the lactase expressing strain originates.

20. The process according to claim 14, wherein said lactase expressing strain has less than 1% of the detectable intracellular or extracellular arylsulfatase activity of the wild type strain from which the lactase expressing strain originates.

21. The process according to claim 14, wherein arylsulfatase activity is undetectable in said lactase expressing strain.

22. The process of claim 1 wherein the yeast is *Kluyveromyces*.

23. The process of claim 22 wherein the yeast is *Kluyveromyces lactis*.

24. The process according to claim 14(c), wherein the gene disruption is achieved by a method selected from one-step gene disruption, marker insertion, site directed mutagenesis, deletion, RNA interference, or anti-sense RNA.

25. The process according to claim 14(c), wherein the lactase expressing cell in which the gene for arylsulfatase is eliminated or disrupted produces more lactase than the wild type cell under the same culture conditions.

* * * * *